US012606849B2

(12) United States Patent
Foody et al.

(10) Patent No.: US 12,606,849 B2
(45) Date of Patent: Apr. 21, 2026

(54) CONVERTING LIGNOCELLULOSIC FEEDSTOCK TO FUEL

(71) Applicant: Iogen Corporation, Ottawa (CA)

(72) Inventors: Brian Foody, Ottawa (CA); Jeffrey S. Tolan, Ottawa (CA); Kristin Martens, Nepean (CA)

(73) Assignee: Iogen Corporation, Ottawa (CA)

( * ) Notice: Subject to any disclaimer, the term of this patent is extended or adjusted under 35 U.S.C. 154(b) by 562 days.

(21) Appl. No.: 17/998,759

(22) PCT Filed: Apr. 23, 2021

(86) PCT No.: PCT/CA2021/050555
§ 371 (c)(1),
(2) Date: Nov. 14, 2022

(87) PCT Pub. No.: WO2021/232143
PCT Pub. Date: Nov. 25, 2021

(65) Prior Publication Data
US 2023/0340543 A1 Oct. 26, 2023

Related U.S. Application Data

(60) Provisional application No. 63/028,888, filed on May 22, 2020.

(51) Int. Cl.
| | |
|---|---|
| *C12P 7/06* | (2006.01) |
| *C08H 8/00* | (2010.01) |
| *C10L 1/02* | (2006.01) |
| *C12P 5/02* | (2006.01) |
| *C12P 19/02* | (2006.01) |
| *C12P 19/14* | (2006.01) |

(52) U.S. Cl.
CPC ................. *C12P 7/06* (2013.01); *C08H 8/00* (2013.01); *C10L 1/02* (2013.01); *C12P 5/026* (2013.01); *C12P 19/02* (2013.01); *C12P 19/14* (2013.01); *C10L 2200/0469* (2013.01); *C10L 2290/10* (2013.01); *C10L 2290/12* (2013.01); *C10L 2290/26* (2013.01); *C12P 2201/00* (2013.01)

(58) Field of Classification Search
CPC .. C12P 7/06; C12P 5/026; C12P 19/02; C12P 19/14; C12P 2201/00; C12P 7/10; C08H 8/00; C10L 1/02; C10L 2200/0469; C10L 2290/10; C10L 2290/12; C10L 2290/26; Y02E 50/10; Y02E 50/30
See application file for complete search history.

(56) References Cited

U.S. PATENT DOCUMENTS

| | | |
|---|---|---|
| 4,168,988 A | 9/1979 | Riehm et al. |
| 4,461,648 A | 7/1984 | Foody |
| 4,908,067 A | 3/1990 | Just |
| 7,198,925 B2 | 4/2007 | Foody |
| 7,503,981 B2 | 3/2009 | Wyman et al. |
| 7,585,652 B2 | 9/2009 | Foody et al. |
| 7,670,813 B2 | 3/2010 | Foody et al. |
| 7,709,042 B2 | 5/2010 | Foody et al. |
| 7,754,457 B2 | 7/2010 | Foody et al. |
| 7,901,511 B2 | 3/2011 | Griffin et al. |
| 7,993,463 B2 | 8/2011 | Griffin et al. |
| 8,101,024 B2 | 1/2012 | Wyman et al. |
| 8,123,864 B2 | 2/2012 | Christensen et al. |
| 8,273,181 B2 | 9/2012 | Foody et al. |
| 8,298,796 B2 | 10/2012 | Tolan et al. |
| 8,328,947 B2 | 12/2012 | Anand et al. |
| 8,404,355 B2 | 3/2013 | Jansen et al. |
| 8,500,910 B2 | 8/2013 | Brady et al. |
| 8,603,789 B2 | 12/2013 | Harlick |
| 8,652,261 B2 | 2/2014 | O'Connor |

(Continued)

FOREIGN PATENT DOCUMENTS

| | | |
|---|---|---|
| WO | WO 2006/026863 | 3/2006 |
| WO | WO 2012/019306 | 2/2012 |

(Continued)

OTHER PUBLICATIONS

Heinone et al, Performance evaluation of a recycle-integrated process for the production and purification of monosaccharides from lignocellulosic mass. Separation and Purification Technol., 2015, vol. 156: 561-571. (Year: 2015).*
Oriez et al., Lignocellulosic Biomass fractionation by mineral acids and resulting extract purification processes: conditions, yields, and purities. Molecules, 2019, vol. 24, 4273, pp. 1-21. (Year: 2019).*
Silva et a., Influence of COD/SO42-ratio on vinasse treatment performance by two-stage anaerobic membrane bioreactor. J. Environ. Management., 2020, vol. 259, 110034, pp. 1-11. (Year: 2020).*
Aslam, Umair et al., "Effect of demineralization on the physiochemical structure and thermal degradation of acid treated indigenous rice husk", Pol. J. of Chem. Tech., vol. 80 (2016), pp. 117-121.
Aston, John E et al., "Performance Assessment of Dilute-Acid Leaching to Improve Corn Stover Quality for Thermochemical Conversion", (2016).

(Continued)

*Primary Examiner* — Ganapathirama Raghu
(74) *Attorney, Agent, or Firm* — Knobbe, Martens, Olson & Bear, LLP

(57) ABSTRACT

A process for converting lignocellulosic biomass to fuel, wherein lignocellulosic feedstock is soaked in a sulfuric acid solution to demineralize the feedstock, the demineralized feedstock is pretreated at a temperature between 150° C. and 230° C. and a pH between 1 and 2.5, at least part of the pretreated material is converted to a fermentation production such as ethanol, and at least a portion of a secondary stream, such as still bottoms from the distillation of ethanol, is converted to biogas by anaerobic digestion. Soaking the lignocellulosic feedstock in sulfuric acid solution reduces the amount of sulfuric acid required for the pretreatment, and thus the amount of sulfate carried downstream to the anaerobic digestion. This increases the biogas yield and/or xylose yield. A recycling process, wherein mineralized soaking liquid produced in the soaking process is fed to cation exchange to remove minerals, reduces excess waste of the sulfuric acid and water usage.

19 Claims, 8 Drawing Sheets

(56) References Cited

U.S. PATENT DOCUMENTS

| | | | |
|---|---|---|---|
| 8,709,770 | B2 | 4/2014 | Harlick et al. |
| 8,785,155 | B2 | 7/2014 | Retsina et al. |
| 8,980,599 | B2 | 3/2015 | Tolan et al. |
| 9,315,427 | B2 | 4/2016 | Foody et al. |
| 9,335,043 | B2 | 5/2016 | Nguyen |
| 9,476,066 | B2 | 10/2016 | Foody |
| 9,493,851 | B2 | 11/2016 | Jansen et al. |
| 9,574,212 | B2 | 2/2017 | Foody et al. |
| 9,783,861 | B2 | 10/2017 | Jansen et al. |
| 9,809,866 | B2 | 11/2017 | Ottonello et al. |
| 9,862,893 | B2 | 1/2018 | Gray et al. |
| 10,179,971 | B2 | 1/2019 | Griffin et al. |
| 10,202,622 | B2 | 2/2019 | Foody et al. |
| 10,336,628 | B2 | 7/2019 | Shi et al. |
| 10,421,667 | B2 | 9/2019 | Foody et al. |
| 10,513,714 | B2 | 12/2019 | Foody et al. |
| 10,612,048 | B2 | 4/2020 | Foody et al. |
| 10,654,235 | B2 | 5/2020 | Miller et al. |
| 10,889,795 | B2 | 1/2021 | Rowland et al. |
| 11,008,598 | B2 * | 5/2021 | Foody .................... D21C 5/005 |
| 2013/0071900 | A1 | 3/2013 | Mackay et al. |
| 2013/0071903 | A1 | 3/2013 | Rowland et al. |
| 2013/0143278 | A1 | 6/2013 | Tolan et al. |
| 2013/0143285 | A1 | 6/2013 | Tolan et al. |
| 2013/0157334 | A1 | 6/2013 | Van Der Heide et al. |
| 2014/0315258 | A1 | 10/2014 | Nguyen |
| 2015/0191758 | A1 | 7/2015 | Larsen et al. |
| 2017/0362618 | A1 | 12/2017 | Nguyen |
| 2018/0355387 | A1 | 12/2018 | Javers et al. |
| 2019/0032094 | A1 | 1/2019 | Yu et al. |
| 2019/0144773 | A1 | 5/2019 | Ribeiro de Lima et al. |
| 2019/0248962 | A1 | 8/2019 | Satlewal et al. |
| 2019/0315636 | A1 | 10/2019 | Shi et al. |
| 2019/0323096 | A1 | 10/2019 | Jansen et al. |

FOREIGN PATENT DOCUMENTS

| | | |
|---|---|---|
| WO | WO2015/142399 A1 | 9/2015 |
| WO | WO2016/113221 A1 | 7/2016 |
| WO | WO 2016/145529 | 9/2016 |
| WO | WO 2017/100907 | 6/2017 |
| WO | WO2017/174093 A9 | 10/2017 |
| WO | WO2019/090413 A1 | 5/2019 |
| WO | WO2019/090414 A1 | 5/2019 |
| WO | WO2019/191828 A1 | 10/2019 |
| WO | WO 2021/232143 | 11/2021 |

OTHER PUBLICATIONS

Bondesson, Pia-Maria et al., "Ethanol and biogas production after steam pretreatment of corn stover with or without the addition of sulphuric acid", Biotechnol Biofuels, vol. 6 (2013), pp. 1-11.

Cesaro, Alessandra et al., "Combined biogas and bioethanol production: Opportunities and challenges for industrial application," Energies, V 8 (2015), pp. 8121-8144.

Horhammer, Hanna et al., "Removal of non-structural components from poplar whole-tree chips to enhance hydrolysis and fermentation performance," Biotechnol Biofuels, V 11 (2018), pp. 1-22.

Humbird, D., "Process design and economics for biochemical conversion of lignocellulosic biomass to ethanol—Dilute-acid pretreatment and enzymatic hydrolysis of corn stover," Technical Report NREL/TP-5100-47764, (2011).

Joelsson, Elisabeth et al., "Combined production of biogas and ethanol at high solids loading from wheat straw impregnated with acetic acid: experimental study and techno-economic evaluation," Sustain Chem Process, vol. 4 (2016), pp. 1-19.

Kang, Qian et al., "Bioethanol from lignocellulosic biomass: current findings determine research priorities," Scientific World Journal, (2014).

Le, Duy Michael, "Biorefining of wheat straw: accounting for the distribution of mineral elements in pretreated biomass by an extended pretreatment-severity equation," Biotechnol Biofuels, V 7 (2014), 1-13.

Luque, Luis, et al., "Comparison of ethanol production from corn cobs and switchgrass following a pyrolysis-based biorefinery approach," Biotechnol Biofuels, V 9 (2016), pp. 1-14.

Mahmood, Hamayoun et al., "Recent advances in the pretreatment of lignocellulosic biomass for biofuels and value-added products," Green and Sustainable Chemistry V 20 (2019) pp. 18-24.

Moraes, Bruna S. et al., "Anaerobic digestion of vinasse from sugarcane ethanol production in Brazil: challenges and perspectives," Renewable and Sustainable Energy Reviews, vol. 44 (2015), pp. 888-903.

Persson, H. et al., "Catalytic pyrolysis of demineralized lignocellulosic biomass," Fuel, V252 (2019) pp. 200-209.

Reza, M. Toufiq, et al., "Ash reduction of corn stover by mild hydrothermal preprocessing," Biomass Conv. Bioref, V 5 (2015), pp. 21-31.

Roeleveld, P.J. et al., "Experience with guidelines for wastewater characterisation in the Netherlands," Water Science and Technology, V 45 (2002) pp. 77-87.

Shan, Lili et al., "Performance of SCTR-EGSB-SBR system for treating sulfate-rich cellulosic ethanol wastewater and microbial community analysis," Environ Sci Pollut Res (2017).

Sluiter, A. et al., "Determination of Ash in Biomass," Technical Report NREL/TP-510-42622 (2008).

Tian, Zhuoli et al., "Anaerobic digestion for treatment of stillage from cellulosic bioethanol production," Bioresource Technology V 144 (2013) pp. 387-395.

Visser, Andre, "The anaerobic treatment of sulfate containing wastewater," Thesis.

Wilkie, Ann C., "Stillage characterization and anaerobic treatment of ethanol stillage from conventional and cellulosic feedstocks," Biomass and Bioenergy V 19 (2000) pp. 63-102.

Written Opinion for PCT/CA2021/050555 dated Jun. 23, 2021.

International Search Report for PCT/CA2021/050555 dated Jun. 23, 2021.

IPRP for PCT/CA2021/050555 dated Nov. 17, 2022.

Sluiter et al., "Determination of Structural Carbohydrates and Lignin in Biomass," NREL Technical Report NREL/TP-510-42618, Aug. 2012, in 18 pages.

European Office Action in EP Application No. 21807899.6 dated Nov. 14, 2023.

Yoon, S.-Y. et al., "The effect of hemicelluloses and lignin on acid hydrolysis of cellulose", Energy, Feb. 2014, vol. 77, pp. 19-24.

European Office Action in EP Application No. 21807899.6 dated Jul. 18, 2025.

* cited by examiner

CONVERTING LIGNOCELLULOSIC FEEDSTOCK TO FUEL

TECHNICAL FIELD

The present invention relates to a system and/or process for converting lignocellulosic feedstock to fuel, and more specifically, relates to a system and/or process for increasing a fraction of the lignocellulosic feedstock converted to fuel.

BACKGROUND

Lignocellulosic biomass is a promising renewable resource for the production of fuels and chemicals. For example, lignocellulosic biomass, which is mainly composed of polysaccharides (i.e., cellulose and hemicellulose) and aromatic polymer (i.e., lignin), can be used to produce products such as ethanol, butanol, and/or biogas without concerns related to using food crops.

Ethanol produced from lignocellulosic biomass is referred to as cellulosic ethanol and can be produced in a production process that includes at least four steps, namely, 1) pretreatment, 2) enzymatic hydrolysis, 3) fermentation, and 4) distillation. Pretreatment is conducted to reduce the recalcitrance of the lignocellulosic biomass to enzymatic hydrolysis. One promising pretreatment is sulfuric acid pretreatment, where the lignocellulosic feedstock is heated with sulfuric acid at elevated temperatures (e.g., greater than 150° C., for under 10 minutes), and where the heat is provided by high pressure steam injected into and/or upstream of the pretreatment reactor. Sulfuric acid pretreatment is generally believed to disrupt the plant cell wall structure (e.g., by hydrolyzing most of the hemicellulose into soluble sugars such as xylose, mannose, arabinose, and glucose), thereby making the lignocellulosic biomass more amenable to enzymatic hydrolysis and/or improving efficiency of the enzymatic hydrolysis (e.g., reducing the enzyme loading, reducing the hydrolysis time, and/or providing an increased cellulose conversion). Enzymatic hydrolysis converts polysaccharides and/or oligomers remaining after pretreatment to fermentable sugars (e.g., cellulose is converted to glucose). Fermentation converts fermentable sugars produced from pretreatment (e.g., xylose and/or glucose) and/or from enzymatic hydrolysis (e.g., glucose) to ethanol using a microorganism (e.g., yeast such as *Saccharomyces cerevisiae*). As will be understood by those skilled in the art, the sugar produced from pretreatment and the sugar produced from enzymatic hydrolysis may be fermented separately or together (i.e., a co-fermentation), depending on the process and/or fermentation microorganism. In addition, as will be understood by one skilled in the art, enzymatic hydrolysis and fermentation can be conducted sequentially or simultaneously. Distillation removes the ethanol from the solution/slurry produced from fermentation. Depending on the process, lignin residues, ash, unreacted cellulose, dissolved hemicellulose, enzymes, and/or microorganisms, can end up in the bottom of a distillation column (i.e., still bottoms).

In general, the high volume and quality of still bottoms from cellulosic ethanol processes can pose serious environmental concerns. For example, with regard to the quality, the still bottoms can have a relatively high chemical oxygen demand (COD) and/or a relatively high biochemical oxygen demand (BOD). One approach to disposing of and/or treating still bottoms is to use a solids/liquid separation to produce a solids stream that is fed to a boiler (e.g., where it is combusted for generating heat and/or electricity), and a liquid stream that is fed to an anaerobic digester, which produces biogas (e.g., which is used for on-site heating, electricity generation, and/or producing fuel). In this approach, the anaerobic digestion of the still bottoms can simultaneously provide wastewater treatment and increase the fraction of the lignocellulosic feedstock converted to fuel (e.g., biogas).

Unfortunately, the use of sulfuric acid ($H_2SO_4$) in pretreatment can produce sulfate ($SO_4^{2-}$) within the process. Elevated sulfate levels are generally believed to have an inhibitory effect on methanogenesis in anaerobic digesters. For example, sulfate can be microbially reduced to sulfide, which is distributed between $H_2S$, $HS^-$, $S^{2-}$ in solution and $H_2S$ in biogas. Hydrogen sulfide ($H_2S$) is generally accepted as a potential inhibitor to the methane-producing bacteria in anaerobic digesters. Moreover, the elevated sulfate levels can introduce a competition for available electron donors (e.g., hydrogen or acetate) between the sulfate-reducing bacteria (SRB) and the methane-producing bacteria (MPB), thereby reducing the methane yield. The importance of this competition can increase with a decrease in the COD to sulfate ratio (e.g., the competition can be more of a concern for higher sulfate levels).

While the anaerobic digestion of sulfate-rich wastewater may pose challenges, it is generally only discussed in terms of ensuring successful operation of the anerobic digester (e.g., ensuring that the anaerobic digester is still able to remove some COD from the wastewater and/or avoiding complete performance failure). More specifically, it is typically discussed in terms of preventing sulfide inhibition. Some approaches proposed for preventing sulfide inhibition include diluting the wastewater, elevating the pH in the reactor, and/or removing sulfide.

SUMMARY

The present disclosure describes one or more embodiments of a method and/or system wherein a lignocellulosic feedstock is pretreated with sulfuric acid as part of a conversion process that converts the lignocellulosic biomass to a fermentation product (e.g., cellulosic ethanol), and wherein one or more secondary streams (e.g., still bottoms) are treated by anaerobic digestion to produce biogas.

The amount of sulfuric acid required for the pretreatment, and thus the amount of sulfate carried downstream to the anaerobic digestion, is reduced by removing an appreciable amount of the minerals from the lignocellulosic feedstock in an acid soaking process conducted upstream of pretreatment. In the acid soaking process, which for example can be a multi-stage countercurrent acid soak, the lignocellulosic feedstock is soaked in a sulfuric acid solution. Advantageously, the sulfuric acid soaking liquid is recycled, thereby reducing excess waste of the sulfuric acid and reducing water usage, while also reducing the amount of sulfuric acid used in the process. The reduced amount of sulfuric acid in pretreatment, which can result in less sulfate in the still bottoms, not only facilitates successful operation of the anaerobic digester, but also facilitates a higher biogas yield and/or a higher xylose yield.

One aspect of the present disclosure is directed to a process for converting lignocellulosic biomass to fuel, said process comprising: (a) a demineralization, said demineralization comprising subjecting a feedstock to an acid soaking process, said feedstock comprising the lignocellulosic biomass, said acid soaking process comprising one or more acid soak stages, wherein each of the one or more acid soak stages comprises (i) contacting the feedstock with a soaking liquid to produce a soaked feedstock slurry, and (ii) subjecting the soaked feedstock slurry to a solids/liquid separation, wherein the soaking liquid in each of the one or more acid soak stages is an aqueous solution comprising sulfuric acid having a pH between 1 and 5; b) a pretreatment, said pretreatment comprising heating a slurry containing sulfuric acid and demineralized feedstock produced from the demineralization, said heating conducted at a temperature between 150° C. and 230° C. and at a pH between 1 and 2.5, said pretreatment producing a pretreated slurry; (c) a first conversion, said first conversion comprising an enzymatic hydrolysis wherein cellulose in the pretreated slurry is converted to glucose, a fermentation wherein the glucose is converted to a fermentation product, and a fermentation product recovery, wherein the first conversion produces a secondary stream that contains one or more sulfur compounds derived from sulfuric acid used in the demineralization, the sulfuric acid used in pretreatment, or a combination thereof; (d) a second conversion, said second conversion comprising feeding at least part of the secondary stream to an anaerobic digester and collecting biogas from the anaerobic digester, said biogas used as a fuel within the process, processed to provide a fuel, or a combination thereof, and (e) a recycling process, said recycling process comprising feeding mineralized soaking liquid produced in step (a) to cation exchange wherein minerals are removed, and feeding clean sulfuric acid solution produced from the cation exchange to one or more acid soak stages.

One aspect of the present disclosure is directed to a process for converting lignocellulosic biomass to fuel, said process comprising: subjecting a feedstock comprising lignocellulosic biomass to a washing process to provide a washed feedstock, subjecting the washed feedstock to an acid soaking process to produce a demineralized feedstock, said acid soaking process comprising a multi-stage countercurrent acid soak, each stage of the multi-stage acid soak comprising (a) contacting the feedstock with an aqueous sulfuric acid solution having a pH not more than 3, and (ii) a solids/liquid separation that provides a pressate and solids, said solids having a consistency of at least 20%, wherein a pressate recycle fraction in at least one stage of the multi-stage countercurrent acid soak is greater than 10% by weight; pretreating the demineralized feedstock to produce a pretreated slurry comprising cellulose, said pretreating comprising heating a slurry containing sulfuric acid and the demineralized feedstock at a temperature between 150° C. and 230° C. and at a pH between 1 and 2.5; converting at least part of the pretreated slurry to a fermentation product, said converting comprising hydrolyzing the cellulose to glucose in an enzymatic hydrolysis, fermenting the glucose to the fermentation product, and recovering the fermentation product in a distillation that produces concentrated ethanol and still bottoms; feeding a stream comprising at least part of the still bottoms to an anaerobic digestion, said stream comprising sulfate derived from sulfuric acid used in the acid soaking process, sulfate derived from sulfuric acid used in pretreatment, or a combination thereof; collecting biogas from the anaerobic digester, said collected biogas used as a fuel within the process, processed to provide a transportation fuel, or a combination thereof; and subjecting mineralized soaking liquid produced from the acid soaking process to cation exchange to remove one or more minerals therefrom and recycling clean sulfuric acid solution produced by cation exchange within the acid soaking process.

One aspect of the present disclosure is directed to a process for converting lignocellulosic biomass to fuel, said process comprising: subjecting a lignocellulosic feedstock to a multi-stage countercurrent water wash to produce a washed feedstock, wherein each stage in the multi-stage countercurrent water wash comprises a solids/liquid separation that provides solids having a consistency of at least 20%; subjecting the washed feedstock to a multi-stage countercurrent acid soak to produce a demineralized feedstock, wherein each stage in the multi-stage countercurrent acid soak comprises a solids/liquid separation that provides solids having a consistency of at least 20%; pretreating the demineralized feedstock to produce a pretreated slurry comprising cellulose, said pretreating comprising heating a slurry containing sulfuric acid and the demineralized feedstock at a temperature between 150° C. and 230° C. and at a pH between 1 and 2.5; converting at least part of the pretreated slurry to a fermentation product, said converting comprising hydrolyzing the cellulose to glucose in an enzymatic hydrolysis, fermenting the glucose to the fermentation product, and recovering the fermentation product in a distillation that produces concentrated ethanol and still bottoms; feeding a stream comprising at least part of the still bottoms to an anaerobic digestion, said stream comprising sulfate derived from sulfuric acid used in the multi-stage countercurrent acid soak, sulfate derived from sulfuric acid used in pretreatment, or a combination thereof; collecting biogas from the anaerobic digester, said collected biogas used as a fuel within the process, processed to provide a transportation fuel, or a combination thereof; and subjecting mineralized soaking liquid produced from the multi-stage countercurrent acid soak to cation exchange to remove one or more minerals therefrom and recycling clean sulfuric acid solution produced by cation exchange to one or more stages in the multi-stage countercurrent acid soak.

One aspect of the present disclosure is directed to a process for converting lignocellulosic biomass to fuel, said process comprising: subjecting a lignocellulosic feedstock to a washing process to provide a washed feedstock, said washing process removing at least 75% of the potassium originally present in the lignocellulosic feedstock and not more than 25% of the calcium originally present in the lignocellulosic feedstock; subjecting the washed feedstock to an acid soaking process to produce a demineralized feedstock, said acid soaking process comprising soaking the washed feedstock in a sulfuric acid solution, said demineralized feedstock containing not more than 30% of the calcium originally present in the feedstock and containing at least 70% of the xylan originally present in the feedstock; pretreating the demineralized feedstock to produce a pretreated slurry comprising cellulose, said pretreating comprising heating a slurry containing sulfuric acid and the demineralized feedstock at a temperature between 150° C. and 230° C. and at a pH between 1 and 2.5; converting at least part of the pretreated slurry to a fermentation product, said converting comprising hydrolyzing the cellulose to glucose in an enzymatic hydrolysis, fermenting the glucose to the fermentation product, and recovering the fermentation product in a distillation that produces concentrated ethanol and still bottoms; feeding a stream comprising at least part of the still bottoms to an anaerobic digestion, said stream comprising sulfate derived from sulfuric acid used in the acid soaking process, sulfate derived from sulfuric acid used in pretreatment, or a combination thereof; collecting biogas from the anaerobic digester, said collected biogas used as a fuel within the process, processed to provide a transportation fuel, or a combination thereof; and subjecting mineralized soaking liquid produced from the acid soaking process to cation exchange to remove one or more minerals therefrom and recycling clean sulfuric acid solution produced by cation exchange to the acid soaking process. In one embodiment, said washing process removes at least 70%, at least 80%, at least 85%, or at least 90% of the potassium originally present in the lignocellulosic feedstock and not more than 5%, not more than 10%, not more than 15%, not more than 20%, or not more than 30% of the calcium originally present in the lignocellulosic feedstock. In one embodiment, said demineralized feedstock contains not more than 5%, not more than 10%, not more than 15%, not more than 20%, or not more than 25% of the calcium originally present in the feedstock and contains at least 75%, at least 80%, at least 85%, or at least 90% of the xylan originally present in the feedstock.

One aspect of the present disclosure is directed to a process for converting lignocellulosic biomass to fuel, said process comprising: subjecting a feedstock to a multi-stage countercurrent acid soak to produce a demineralized feedstock, said feedstock comprising a lignocellulosic feedstock from which at least 75% of the potassium originally present in the lignocellulosic feedstock has been removed; pretreating the demineralized feedstock to produce a pretreated slurry comprising cellulose, said pretreating comprising heating a slurry containing sulfuric acid and the demineralized feedstock at a temperature between 150° C. and 230° C. and at a pH between 1 and 2.5; converting at least part of the pretreated slurry to a fermentation product, said converting comprising hydrolyzing the cellulose to glucose in an enzymatic hydrolysis, fermenting the glucose to the fermentation product, and recovering the fermentation product in a distillation that produces concentrated ethanol and still bottoms; feeding a stream comprising at least part of the still bottoms to an anaerobic digestion, said stream comprising sulfate derived from sulfuric acid used in the multi-stage countercurrent acid soak, sulfate derived from sulfuric acid used in pretreatment, or a combination thereof; collecting biogas from the anaerobic digester, said collected biogas used as a fuel within the process, processed to provide a transportation fuel, or a combination thereof; and subjecting mineralized soaking liquid produced from the multi-stage countercurrent acid soak to cation exchange to remove one or more minerals therefrom and recycling clean sulfuric acid solution produced by cation exchange to one or more stages in the multi-stage countercurrent acid soak.

6

DETAILED DESCRIPTION

Figure 1:
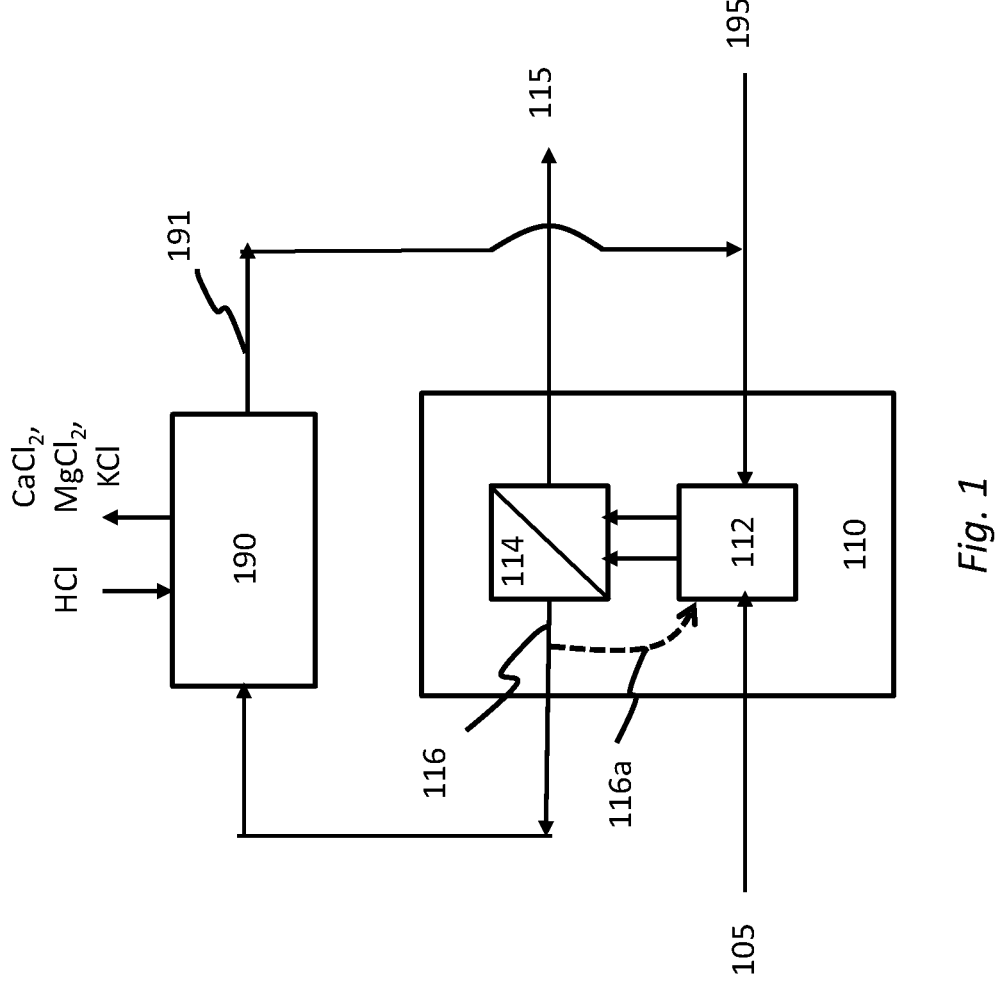
FIG. 1 is a flow diagram illustrating an embodiment of a single stage acid soak.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The term "between" as used herein in the context of ranges is intended to include the endpoints of the indicated ranges, for example, a value that is "between 2 and 5" includes not only the intermediate values but the endpoints "2" and "5" as well. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. The terms "first", "second", etc., may be used to distinguish one element from another, and these elements should not be limited by these terms. In the context of describing the combining of components by the "addition" or "adding" of one component to another, or the separating of components by the "removal" or "removing" of one component from another, those skilled in the art will understand that the order of addition/removal is not critical (unless stated otherwise). Unless defined otherwise, all technical and scientific terms used herein have the same meanings as commonly understood by one of ordinary skill in the art.

The term "sulfate", as used herein, refers to the sulfate ion ($SO_4^{2-}$) or any salts containing the sulfite ion (i.e., sulfate salts).

The term "mineral", as used herein, refers to elements selected from sodium (Na), potassium (K), calcium (Ca), magnesium (Mg), iron (Fe), and aluminum (Al), which can be present in the lignocellulosic feedstock as salts.

The term "demineralized feedstock", as used herein, refers to lignocellulosic biomass from which one or more minerals have been removed (e.g., as salts).

The term "mineralized soaking liquid", as used herein, refers to an aqueous solution containing sulfate salts produced by dissolving one or more minerals from a lignocellulosic feedstock into an aqueous solution containing sulfuric acid.

The terms "remove", "removing", and "removal", as used herein with reference to one or more minerals, includes partial removal of one or more minerals.

The term "countercurrent acid soak", as used herein, refers to a multi-stage acid soaking process wherein pressed soaking liquid from a downstream soak is used in an upstream soak.

The terms "upstream" and "downstream", as used herein, refer to the disposition of a step/stage in the process with respect to the disposition of other steps/stages of the process. For example, the term upstream can be used to describe to a step/stage that occurs at an earlier point of the process, whereas the term downstream can be used to describe a step/stage that occurs later in the process.

The term "secondary stream", as used herein, refers to a stream that branches off from and/or is otherwise sourced from the main stream that provides the primary product of the process (e.g., of the first conversion process).

The term "pressate recycle fraction", as used herein for a given soaking/washing stage, refers to the weight fraction of the liquid produced by the solids/liquid separation (e.g., pressate or filtrate) in that stage that is retained for soaking/washing purposes within that stage.

The term "continuous stirred vessel", as used herein, refers to a vessel that is configured to provide agitation and permit continuous operation (i.e., a continuous feed and continuous product withdrawal). For example, a continuous stirred vessel typically includes separate inlets and outlets to allow simultaneous inputs and outputs of tank contents. The term "continuous operation" or "continuous mode", as used herein, denotes that the operation ordinarily proceeds without significant interruption in time and/or can approach steady-state conditions. Continuous operation can include interruptions if of a duration that does not disrupt steady-state conditions.

The terms "soak" and "soaking", as used herein, generally refers to adding a liquid to solids (or solids to liquid) to wet the solids such that at least a portion of the liquid penetrates, permeates, and/or impregnates the solids and/or such that the solids absorb at least some of the liquid. Soaking may or may not achieve saturation of the solids.

The present invention is directed to a system and/or process for converting lignocellulosic feedstock to fuel, and more specifically, to a system and/or method for increasing a fraction of lignocellulosic feedstock converted to fuel.

In accordance with the present invention, a process is provided that includes the following:

a. demineralization of a lignocellulosic feedstock including an acid soaking process;

b. sulfuric acid pretreatment;

c. a first conversion process that includes enzymatic hydrolysis and fermentation to produce a fermentation product;

d. a second conversion process that includes anaerobic digestion of a secondary stream produced from the first conversion process; and e. a recycling process, said recycling process comprising feeding mineralized soaking liquid produced in step (a) to cation exchange.

Lignocellulosic feedstocks can have a significant inorganic content (e.g., potassium, sodium, calcium, magnesium, iron, aluminum, phosphorus, manganese, and/or zinc). In general, minerals such as potassium, sodium, calcium, magnesium, iron, and aluminum can be present in lignocellulosic biomass as salts (e.g., carbonate or oxalate salts). These salts can neutralize some of the sulfuric acid and/or have a buffering effect during sulfuric acid pretreatment, which can increase the amount of sulfuric acid required for pretreatment (e.g., on weight percent of dry feedstock). Washing or leaching the lignocellulosic feedstock can remove some of the minerals (e.g., remove some water-soluble potassium salts). However, the amount of sulfuric acid required to bring a slurry containing the lignocellulosic feedstock to a pH between about 1.0 and 1.8 can still be quite high, even after a thorough washing of the lignocellulosic feedstock with water. Using large amounts of acid in pretreatment adds to the cost of the process.

In U.S. Pat. No. 7,503,981, there is disclosed a method for removing minerals from a cellulosic biomass that includes prewashing the biomass with an acid solution followed by a wash with water. While this patent indicates that less $H_2SO_4$ is required to produce a given amount of ethanol (e.g., a ⅓ reduction in acid use), the method disclosed therein generates a significant amount of sulfate salt, which can be costly to dispose of, and can have a higher water consumption. It does not address the technical concerns related to and/or provide solutions to large amounts of sulfate produced by the process.

In the system and/or process disclosed herein, the lignocellulosic feedstock is treated in a demineralization process, wherein the feedstock is subjected to an acid soaking process that includes one or more acid soak stages (e.g., a multi-stage acid soak). Each acid soak stage includes i) contacting the lignocellulosic feedstock with a soaking liquid, and ii) a solids/liquid separation. The soaking liquid in each acid soak stage is an aqueous sulfuric acid solution. The solids/liquid separation in each acid soak stage separates at least part of the feedstock from at least a portion of the soaking liquid, typically by applying a force (e.g., a pushing force, such as pressing or squeezing) in order to force liquid out of the solids.

Advantageously, the process recycles at least part of the soaking liquid from the acid soaking process after removing minerals therefrom using cation exchange. Accordingly, the acid soaking process disclosed herein produces less sulfate waste and/or requires minimal water consumption (e.g., some make-up water and/or make-up sulfuric acid solution may be added).

Further advantageously, the acid soaking process disclosed herein does not require a water wash to reach a low mineral content. Rather, a relatively low mineral content can be achieved in one or more additional acid soak stages. In each acid soak stage, the feedstock is soaked in a soaking liquid (i.e., a sulfuric acid solution). During this acid soak, the feedstock is soaked in the soaking liquid and minerals in the feedstock (e.g., present as salts) are dissolved in the soaking liquid. The solids/liquid separation separates the sulfuric acid soaked feedstock from at least a portion of the soaking liquid, thereby providing a solids stream comprising demineralized feedstock and a liquid stream comprising mineralized soaking liquid. Since the solids stream retains some of the mineralized soaking liquid (i.e., is not 100% dry), some minerals remain. In a second acid soak, the minerals that remain are diluted such that, after a second solids/liquid separation, significant mineral removal occurs. In addition to reducing the mineral concentration (e.g., by dilution), the second acid soak can dissolve more minerals, particularly if it is conducted a lower pH. Since a portion of the soaking liquid remains with and/or impregnated within the demineralized feedstock after the second solids/liquid separation (i.e., is not washed away), a more uniform acid impregnation is achieved for pretreatment. In general, uniform acid impregnation in pretreatment can ensure that some parts of the feedstock are not overcooked and/or degraded due to high localized concentration of the acid, and/or that some parts of the feedstock are not undercooked (e.g., which may result in low xylose yield and incomplete cellulose hydrolysis). Undercooking or overcooking of lignocellulosic feedstock can be particularly problematic when the pretreatment is conducted under medium or high solids consistency since the non-uniformity in the concentration of the acid and the temperature may be more pronounced. Providing a more uniform acid impregnation is beneficial for the process described herein, particularly in view of the reduced sulfuric acid required for pretreatment (i.e., as a result of the reduced mineral content) and/or the possibility of a faster pretreatment time resulting from an improved pretreatment (e.g., associated with a lower amount of minerals). Moreover, the process described herein facilitates pretreating at higher consistencies since supplemental acid is not necessarily required.

Since the demineralization reduces the amount of one or more minerals in the lignocellulosic feedstock, and thus reduces the amount of sulfuric acid required for pretreatment, and potentially carried through to anaerobic digestion, the biogas yield can be increased in the second conversion process. Accordingly, a larger fraction of the lignocellulosic feedstock can be converted to fuel and/or chemical.

Feedstock

In general, the feedstock can include any suitable lignocellulosic biomass. Lignocellulosic biomass refers to biomass containing cellulose, hemicellulose, and lignin. Lignocellulosic biomass typically has cellulose in an amount greater than about 25%, hemicellulose in an amount greater than about 15%, and lignin in an amount greater than 15% lignin, by weight (w/w). In one embodiment, the feedstock has a combined content of cellulose, hemicellulose and lignin greater than 25% (w/w). In one embodiment, the feedstock is a mixture of particles that originate from different kinds of lignocellulosic biomass.

In one embodiment, the feedstock includes a biomass crop such as a grass (e.g., switch grass, energy cane, sorghum (including sweet sorghum), cord grass, rye grass, *miscanthus*, reed canary grass, and/or *Arundo donax*). In one embodiment, the feedstock includes a residue, byproduct, and/or waste from a biorefinery (e.g., sugar cane bagasse, sugar cane tops and leaves, beet pulp, Jerusalem artichoke residues, corn fiber, corn stover, and/or bran from grains). In one embodiment, the feedstock includes an agricultural residue (e.g., soybean stover, corn stover, rice straw, sugar cane tops and/or leaves, rice hulls, barley straw, corn cobs, wheat straw, canola straw, oat straw, oat hulls, corn fiber, and/or corn cobs). The term "straw", as used herein, refers to the stem, stalk and/or foliage portion of crops remaining after the removal of starch and/or sugar containing components for consumption. Examples of straw include, but are not limited to, sugar cane tops and/or leaves, bagasse, oat straw, wheat straw, rye straw, oat straw, rice straw and barley straw. The term "stover", as used herein, includes the stalk and foliage portion of crops after the removal of starch and/or sugar containing components of plant material for consumption. Examples of stover include, but are not limited to, soy bean stover, sorghum stover, and corn stover. In one embodiment, the feedstock includes forestry biomass (e.g., recycled wood pulp fiber, sawdust, hardwood, softwood, trimmings and/or slash from logging operations). In one embodiment, the feedstock includes municipal waste (e.g., post-consumer material or waste from a variety of sources such as domestic, commercial, institutional and/or industrial sources). In one embodiment, the feedstock is sugar cane.

As described herein, the process of the present invention may be particularly beneficial when the feedstock has a significant ash content. The term "ash", as used herein, has its ordinary meaning as known to those skilled in the art, and generally refers to the material that remains following complete combustion of the biomass. Ash, which can be present in the feedstock as various minerals can be physiological ash (i.e., bound within the cells and/or cell walls) and/or entrained ash (e.g., from sand, soil and/or fertilizers).

In general, the amount of ash (w/w) and composition of the ash can vary with the type of feedstock and/or feedstock handling procedures. Some examples of feedstock that can have a relatively high ash content include wood, rice hulls, straw, and switchgrass. In one embodiment, the feedstock is primarily wood (e.g., softwood or hardwood), straw (e.g., wheat, oat, or barley), or residues (e.g., corn stover or bagasse). In one embodiment, the feedstock is primarily wheat straw, rice hulls, corn stover, or switchgrass.

The presence of ash in lignocellulosic feedstocks, particularly inorganic salts such as potassium salts, is known to increase chemical consumption in acid pretreatment due to its buffering and/or neutralizing effect. It is known to remove ash from feedstocks such as wheat straw by leaching with an aqueous solution prior to chemical treatment as described in U.S. Pat. No. 7,901,511 (Griffin et al.). While leaching can reduce chemical demand, it can consume significant amounts of water.

Some minerals such as calcium, magnesium, iron, and aluminum may not be readily released from lignocellulosic feedstock with a water wash. For example, calcium and/or magnesium can be present in lignocellulosic biomass as salts (e.g., carbonate or oxalate salts) that are relatively insoluble at neutral pH values but can be more soluble at lower pH values. As described herein, the process of the present invention may be particularly advantageous when the feedstock has a significant mineral content, where at least some of the minerals are relatively insoluble at neutral pH values, and/or when the feedstock has a significant calcium and magnesium content.

In one embodiment, the lignocellulosic feedstock contains more than about 1%, more than about 2%, more than about 3%, more than about 4%, or more than about 5% ash by dry weight (% wt/wt). In one embodiment, the lignocellulosic feedstock contains between about 2% and about 8% ash, by weight. In these embodiments, the amount of ash in the lignocellulosic feedstock is determined in accordance with NREL/TP-510-42622.

In one embodiment, the feedstock contains at least 1 mg, at least 2 mg, at least 3 mg, at least 4 mg, at least 5 mg, at least 6 mg, at least 7 mg, at least 8 mg, at least 9 mg, or at least 10 mg of minerals, in aggregate, per gram of dry feedstock. In one embodiment, the feedstock contains at least 1 mg, at least 2 mg, or at least 3 mg of magnesium and calcium, in an aggregate, per gram of dry feedstock. In one embodiment, the feedstock contains at least 1 mg, at least 2 mg, at least 3 mg, at least 4 mg, or at least 5 mg of potassium per gram of dry feedstock. In one embodiment, the feedstock contains at least 1 mg or at least 2 mg of calcium per gram of dry feedstock. In one embodiment, the feedstock contains at least 1 mg of magnesium per gram of dry feedstock. The amount of each mineral originally present in the feedstock is determined using inductively coupled plasma-optical emission spectrometry (ICP-OES).

In general, feedstock preparation can include subjecting the feedstock to any preparatory steps and/or handling techniques known in the art. For example, feedstock preparation can include receiving the feedstock (e.g., delivered by truck), storing the feedstock (e.g., short term queuing and/or for off-season use), weighing the feedstock, and/or one or more steps to standardize its physical and/or chemical characteristics (e.g., improving uniformity of the feedstock). Some steps to standardize its physical and/or chemical characteristics can include monitoring and/or adjusting the water content of the feedstock (e.g., prior, during, and/or after storage), removing debris from the feedstock (e.g., removing sand and/or rocks), and/or size reduction. As will be understood by those skilled in the art, some of these feedstock preparation steps can be optional and may be dependent on the type of lignocellulosic biomass, the feedstock supplier, the selected pretreatment conditions, and/or the specific processing plant. For example, some processing plants may arrange to receive feedstock that is pre-processed and/or homogenized to some degree before delivery. Feedstock preparation for fiber feedstock, such as wheat straw, can include bale breaking, cutting, and/or depithing or dedusting.

In one embodiment, feedstock preparation includes size reduction. Some examples of size reduction methods include milling, grinding, cutting, agitation, shredding, chipping, compression/expansion, and/or other types of mechanical action. Size reduction by mechanical action may be performed by any type of equipment adapted for the purpose, for example, but not limited to, hammer mills, tub-grinders, roll presses, refiners, and hydrapulpers. As will be understood by those skilled in the art, the size reduction technique and/or degree may be selected in dependence upon the feedstock and the process (e.g., type of pretreatment, size of the pretreatment reactor, and/or method of conveying the feedstock within the process). For example, woody feedstock is often treated as particles having a width/length between 2 mm and 50 mm, whereas feedstock that inherently has one narrow dimension (e.g., straw) is often treated as particles having a length between 2 mm and 150 mm. In one embodiment, feedstock having an average particle size that is greater than about 150 mm to 200 mm is subject to a size reduction wherein at least 90% by volume of the particles produced from the size reduction have a length between about 2 mm and about 150 mm. Some examples of suitable size reductions and/or equipment are described in WO 2006/026863.

In one embodiment, at least 80% of the feedstock has a particle length between about 2 cm and about 40 cm, between about 2 cm and about 30 cm, or between about 2 cm and 20 cm.

In one embodiment, feedstock preparation includes sand removal. For example, sand may be removed using other wet or dry sand removal techniques that are known in the art (e.g., including the use of a hydrocyclone or a sieve).

Demineralization

Lignocellulosic feedstock typically contains minerals. While some minerals such as potassium and sodium can be present as salts that are largely removed with sufficient washing or leaching with water, other minerals such as calcium and magnesium can be present in the lignocellulosic feedstock as salts that are insoluble at substantially neutral pH values.

Soaking the lignocellulosic feedstock in a sulfuric acid solution can remove some of these minerals that are difficult to remove at neutral pH values. More specifically, it has been found that if the pH is sufficiently low, minerals such as calcium and magnesium present in the lignocellulosic feedstock can be dissolved, and a portion thereof separated from the lignocellulosic feedstock in a solids/liquid separation.

As described herein, the process includes a demineralization that includes an acid soaking process, which can be proceeded by an optional washing process. The acid soaking process includes one or more soak stages, wherein each acid soak stage includes:

1. contacting the feedstock with a soaking liquid, and
2. a solids/liquid separation, wherein the feedstock is separated from at least a portion of the soaking liquid.

The soaking liquid in each stage is an aqueous solution comprising sulfuric acid. The conditions (e.g., pH, temperature, duration, consistency) for each acid soaking step in the acid soaking process (i.e., step (i) of contacting the feedstock with a soaking liquid) are selected to dissolve a sufficient amount of minerals (i.e., in aggregate for the acid soaking process), including a sufficient amount of calcium and/or magnesium, without substantially hydrolyzing hemicellulose or cellulose in the feedstock (e.g., less than about 20% of hemicellulose). In one embodiment, less than 15%, less than 14%, less than 13%, less than 12%, less than 11%, less than 10%, less than 9%, less than 8%, less than 7%, less than 6%, less than 5%, less than 4%, less 3%, less than 2%, or less than 1%, by weight, of the hemicellulose present in the lignocellulosic feedstock is dissolved in the acid soaking process.

In general, in each acid soaking step, the pH is between about 1 and about 5, the temperature is between about 10° C. and about 95° C., the contact time is between about 2 minutes and about 60 minutes, and the consistency is between about 2% and about 12%. When the acid soaking process includes more than one stage, the different stages may have the same or different conditions (i.e., pH, temperature, duration, consistency) in each acid soaking step.

In one embodiment, the pH in each soaking acid step is between about 1.1 and about 4, between about 1.1 and about 3.5, between about 1.1 and about 3, between about 1.2 and about 4, between about 1.2 and about 3.5, between about 1.3 and about 3, between about 1.3 and about 4, between about 1.4 and about 3, between about 1.6 and about 3, or between about 1.6 and about 2.5. In one embodiment, the soaking liquid in at least one acid soaking step is between about 1.3 and about 2, between about 1.4 and about 2, between about 1.5 and about 2, or between about 1.6 and about 2. Providing a multi-stage soaking process, wherein one or more of the acid soaking steps is at a pH between about 1.3 and about 3.5 has been found to effectively dissolve calcium and magnesium from lignocellulosic feedstock. In addition, it has been found that providing a multiple stage acid soak, wherein the acid soaking step in the first stage has a higher pH than the acid soaking step in the final stage, can have one or more advantages. For example, the equipment (e.g., tanks and/or presses) used at low pH values (e.g., less than about 3) can require corrosion resistant metallurgy (e.g., Incoloy, Hastelloy), which can increase costs. Providing a multi-stage acid soaking process where a higher pH (e.g., about 3 or above) is used for the acid soaking step(s) in early stages can facilitate using less expensive equipment for at least part of the acid soaking process (e.g., for half the equipment).

In one embodiment, the temperature in each acid soaking step is between about 20° C. and about 90° C., between about 30° C. and about 90° C., between about 25° C. and about 85° C., between about 30° C. and about 80° C., between about 40° C. and about 90° C., between about 40° C. and about 80° C., or between about 50° C. and about 80° C. Advantageously, providing a multi-stage soaking process, wherein one or more of the acid soaking steps is at a temperature between 40° C. and 80° C. has been found to effectively dissolve calcium and magnesium from lignocellulosic feedstock. Moreover, a temperature between 40° C. and 80° C. facilitates using shorter contact times in each stage, such that the total contact time (i.e., sum from all stages) is a reasonable duration. In one embodiment, the soaking temperature in each of the one or more stages is between about 40° C. and about 60° C.

In one embodiment, the contact time in each acid soaking step is at least 1 minute, at least 2 minutes, at least 3 minutes, at least 4 minutes, at least 5 minutes, or at least 10 minutes. In one embodiment, the contact time in each acid soaking step is between about 1 minute and about 5, 10, 15, 20, 25, 30, 35, 40, or 45 minutes. In one embodiment, the contact time in each acid soaking step is between about 2 minute and about 5, 10, 15, 20, 25, 30, 35, 40, or 45 minutes. In one embodiment, the contact time in each acid soaking step is between about 3 minutes and about 5, 10, 15, 20, 25, 30, 35, 40, or 45 minutes. In one embodiment, the contact time in each acid soaking step is between about 4 minutes and about 5, 10, 15, 20, 25, 30, 35, 40, or 45 minutes. In one embodiment, the contact time in each acid soaking step is between about 5 minutes and about 5, 10, 15, 20, 25, 30, 35, 40, or 45 minutes. A contact time of about 30 minutes at about 50° C. can allow the system to reach equilibrium in a single stage soak.

In one embodiment, the acid soaking process is a multi-stage acid soaking process and the total contact time throughout the acid soaking process (i.e., sum of the contact times from the multiple stages) is between about 5 minutes and about 10, 15, 20, 25, 30, 35, 40, 45, 50, 55, or 60 minutes. Advantageously, providing a multi-stage soaking process, wherein the soaking temperature(s) are between 40° C. and 80° C., the pH is between 1.3 and 4, and the total contact time is between 5 and 20 minutes, can effectively dissolve calcium and magnesium from lignocellulosic feedstock (e.g., remove more than 80%, more than 85%, more than 90%, or about 95% of the calcium from the lignocellulosic feedstock).

In general, the acid soaking step in each stage is conducted in relatively dilute conditions. In one embodiment, the consistency in each acid soaking step is less than about 5%, less than about 6%, less than about 7%, less than about 8%, less than about 9%, less than about 10%, or less than about 11%. In one embodiment, the consistency in each acid soaking step is between about 2% and about 5%, about 6%, about 7%, or about 8%. In one embodiment, the consistency in each acid soaking step is between about 2.5% and about 6.5%. In one embodiment, the consistency in each acid soaking step is between about 3% and about 5%. Providing a consistency of at least 3% and not more than 5% can be particularly suitable. The term "consistency", as used herein, refers to the mass of undissolved dry solids or "UDS" in a sample per mass of the sample, expressed as a weight percent (e.g., wt %). The mass of undissolved solids can be determined by filtering and washing the sample to remove dissolved solids and then drying the sample at a temperature and for a period of time that is sufficient to remove water from the sample, but does not result in thermal degradation of the sample.

The conditions in each acid soaking step (e.g., pH, temperature, duration, and/or consistency) are selected to dissolve a sufficient amount of minerals (i.e., in aggregate for the acid soaking process), without substantially hydrolyzing hemicellulose or cellulose in the feedstock. Accordingly, as will be understood by those skilled in the art, each condition may be selected in dependence upon the other conditions used for the acid soaking process including, for example, the degree of agitation. For example, a higher temperature may be combined with a shorter contact time. Appropriate selection of the conditions will be to those skilled in the art having the benefit of the teachings herein.

In general, the acid soaking process can be co-current or countercurrent, and each acid soaking step can be conducted in batch mode, semi-continuous mode, or continuous mode, with or without agitation, using any suitable equipment known in the art. Some examples of soaking equipment include, but are not limited to, vats, continuous stirred vessels (e.g., functions as a continuous stirred tank reactor or CSTR), washing drums, tubular reactors (e.g., functions as a plug flow reactor or PFR), and screw conveyers. Other examples include solid/liquid extraction or leaching equipment, which for example, may be used in the pulp and paper industry. Continuous operation, as for example offered by a continuous stirred vessel, provides advantages of continuous production and a steady state of operation once the reactor is running. Agitation, as for example offered by impellers and/or baffles, increases mass transfer and/or increases uniformity. In one embodiment, one or more of the soaking steps are conducted using continuous operation. In one embodiment, one or more of the soaking steps are conducted using an agitated system. In one embodiment, one or more of the soaking steps use a continuous stirred vessel.

In each acid soak stage, after the lignocellulosic feedstock has contacted the soaking liquid and produced a soaked feedstock slurry wherein minerals from the feedstock are dissolved in the soaking liquid, the soaked feedstock slurry is subjected to a solids/liquid separation. In each solids/liquid separation, an undissolved part of the feedstock is separated from at least a portion of the soaking liquid to produce solids containing demineralized feedstock and mineralized soaking liquid.

In general, each solids/liquid separation can be conducted in continuous mode or batch mode, using any suitable solids/liquid technologies or combination of technologies known in the art. Solids/liquid separations are well known, and typically use an applied force (e.g., gravity, centrifugal, pressure) to separate at least a portion of the liquid from the solids. For example, some non-limiting examples of equipment for conducting solids/liquid separations include drainers, filters, screens, centrifuges, rotary presses (roll presses), inclined screws, extruders, belt presses, filter presses, screw presses, etc.

As will be understood by those skilled in the art, the solids/liquid equipment may be selected in dependence upon the feedstock, the consistency of the soaked feedstock slurry, and the desired final consistency. In one embodiment, each solids/liquid separation provides solids (e.g., slurry and/or wet cake) having a consistency of at least about 12%, at least about 15%, at least about 18%, at least about 20%, at least about 22%, at least about 24%, at least about 25%, at least about 28%, or at least about 30%. In one embodiment, the solids/liquid separator in at least one acid soak stage is a dewatering screw press that provides solids having a consistency between about 24% and about 28%.

When the acid soaking process includes more than one stage, the solids/liquid separations in different stages may have the same or different conditions, and/or may use the same or different technologies. For example, using a solids/liquid separation that provides solids having a consistency of at least 15% (e.g., preferably between about 24% and about 28%) in one or more of the early stages of the acid soaking process is advantageous in that more liquid, and thus more minerals, are removed, thereby facilitating removing even more minerals in a subsequent stage. Using a solids/liquid separation that provides solids having a consistency greater than about 18% (e.g., preferably between about 24% and about 28%) in the final stage is advantageous in that the pretreatment can be conducted at a relatively high consistency (e.g., even when additional sulfuric acid is added). Providing a solids/liquid separation that can operated under high pressure conditions (e.g., higher than 30 psig) can be advantageous when the solids are discharged directly into the pretreatment reactor or directly into a chamber or conduit in fluid communication with the pretreatment reactor (e.g., which is typically pressurized). In one embodiment, one or more early acid soak stages use a dewatering screw press that provides solids having a consistency of at least 24%, whereas the final stage (just upstream of pretreatment) uses a pressurized screw press providing a demineralized feedstock having a consistency of at least 24%.

In general, increased mineral removal is provided when the solids/liquid separation(s) in the acid soaking process applies a pressure to separate the liquids and solids. For example, when the solids/liquid separation presses or squeezes the solids, more liquid can be forced out of the feedstock and removed therefrom. Solids/liquid separation equipment based on pressing and/or squeezing is known to those skilled in the art. For example, some non-limiting examples include a screw press, an extruder, a roll press, a filter press, a belt press, and a plate press, etc. In one embodiment, the solid liquid separation includes a screw press (e.g., a dewatering screw press). Screw presses are well known in the art. Using a screw press to provide the solids/liquid separation is advantageous because typically they can effectively dewater slurries having a consistency of about 3%-12% to yield solids having a consistency up to about 30%.

Referring to FIG. 1, there is shown a simplified flow diagram of an acid soaking process in accordance with one embodiment. In this embodiment, the feedstock 105 is provided to a single stage soaking process 110 that includes a first step 112 in which the feedstock is contacted with the soaking liquid to provide a soaked feedstock slurry, and a second step 114 in which the feedstock is separated from at least a portion of the soaking liquid to produce solids containing demineralized feedstock 115 (e.g., pressed cake) and mineralized soaking liquid 116 (e.g., pressate). At least a portion of the mineralized soaking liquid 116, which contains dissolved minerals (e.g., contains calcium and/or magnesium cations), is subjected to a cation exchange 190. Optionally, a portion 116a of the mineralized soaking liquid, is reused directly within the first step 112. In the cation exchange 190, positively charged cations in the mineralized soaking liquid (e.g., $K^+$, $Ca^{2+}$ and/or $Mg^{2+}$) are exchanged for hydrogen ($H^+$) from a strong acid such as hydrochloric acid (HCl), thereby producing salts (e.g., potassium chloride, calcium chloride, and/or magnesium chloride) and a clean sulfuric acid solution 191. The term "clean sulfuric acid solution", as used herein, refers to a sulfuric acid solution from which one or more minerals (e.g., potassium, calcium and/or magnesium cations) have been removed. The clean sulfuric acid solution 191 is recycled within the process for use in the acid soak step 112 (optionally with make-up sulfuric acid 195).

Figure 2A:
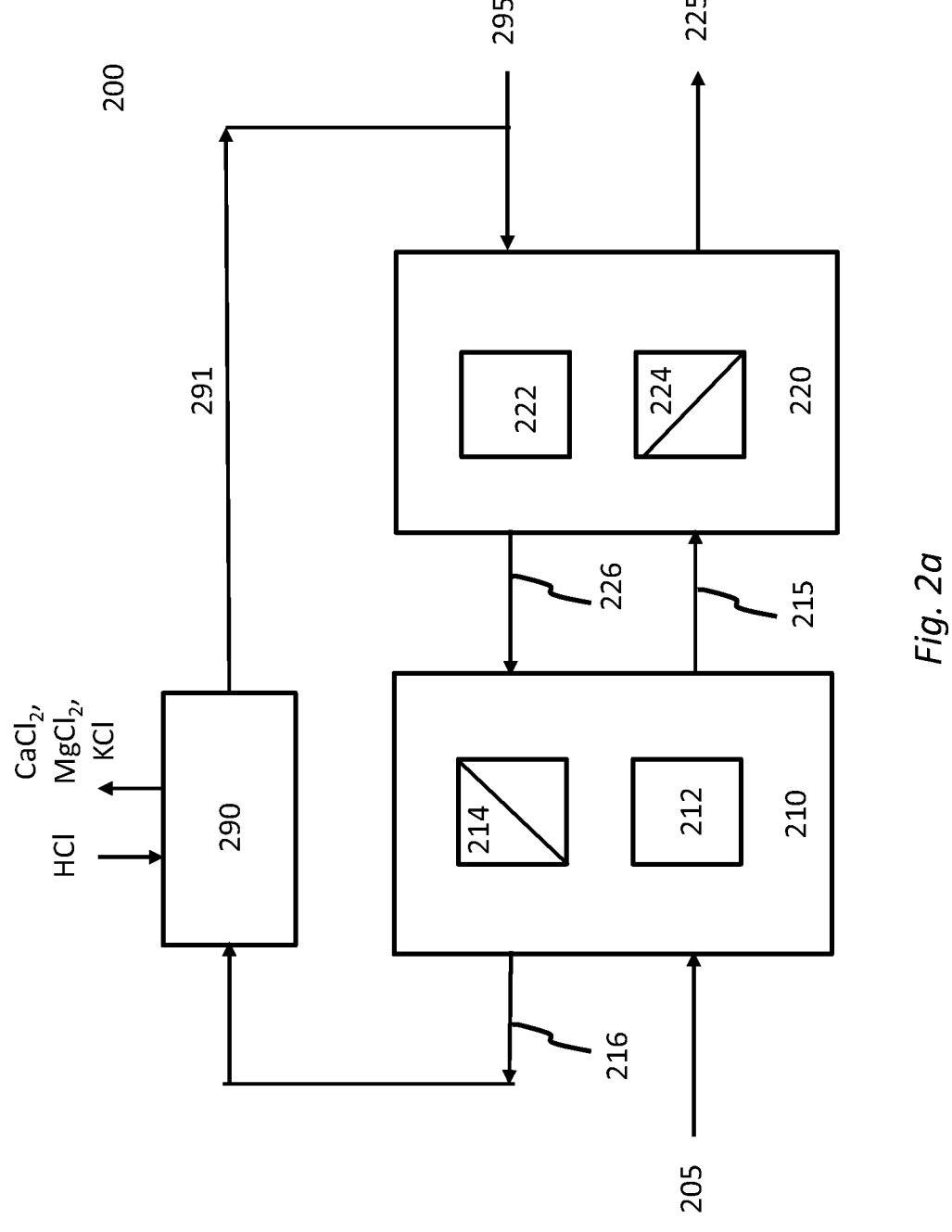
FIG. 2*a* is a flow diagram illustrating an embodiment of a two-stage acid soak.

Referring to FIG. 2a, there is shown a flow diagram of an acid soaking process in accordance with one embodiment. In this embodiment, the feedstock 205 is fed to a two-stage soaking process 200 that includes a first stage 210 and a second stage 220. The first stage 210 includes a first step 212 in which the feedstock is contacted with soaking liquid (i.e., a sulfuric acid solution) to provide a soaked feedstock slurry, and a second step 214 in which the soaked feedstock slurry is subjected to a solids/liquid separation. The solids/liquid separation separates the acid impregnated feedstock from at least a portion of the soaking liquid, thereby producing a solids stream 215 containing demineralized feedstock (e.g., pressed cake) and a liquids stream 216 containing mineralized soaking liquid (e.g., pressate).

The mineralized soaking liquid 216, which contains dissolved minerals (e.g., contains calcium and/or magnesium cations), is subjected to a cation exchange 290 to produce clean sulfuric acid solution 291. The solids stream 215 is contacted with soaking liquid in a first step 222 of the second stage 220 to produce a soaked feedstock slurry, which is subjected to a solids/liquid separation 224, thereby producing a solids stream 225 that contains demineralized feedstock and liquid stream 226 that contains mineralized soaking liquid.

In this embodiment, at least part of the liquid stream 226 from the second stage 220 is used in the first acid soak stage 212. Accordingly, this embodiment is referred to as a multi-stage, countercurrent acid soak. A countercurrent acid soak has the advantage that the solids 215 produced by the first stage 210 are re-soaked in cleaner soaking liquid, thereby further improving mineral removal. For example, the soaking liquid for the second step 222 includes clean sulfuric acid 291 from the cation exchange, and typically includes some make-up sulfuric acid 295. Furthermore, a countercurrent acid soak is more efficient for cation exchange. For example, in addition to using less sulfuric acid solution, the countercurrent acid soak provides a relatively high concentration of minerals in the mineralized soaking liquid 216 fed to cation exchange 290.

As will be apparent to those skilled in the art, the flow direction of soaking liquid between stages and/or the source of sulfuric acid in each soak stage for the processes disclosed herein can vary. In one embodiment, the acid soaking process is a multi-stage, countercurrent acid soak. In one embodiment, the acid soaking process is a multi-stage, co-current acid soak. In one embodiment, the acid soaking process is a multi-stage, countercurrent acid soak, wherein each soaking step receives sulfuric acid from cation exchange and/or recycles part of the pressate/filtrate within that stage.

In one embodiment, the acid soaking process is a multi-stage, countercurrent acid soaking process, wherein for one or more stages, between about 5% and about 95%, between about 5% and about 80%, between about 5% and about 70%, between about 5% and about 60%, or between about 5% and about 50% of the pressate/filtrate produced in a stage is recycled within that stage. Recycling pressate/filtrate within a stage is advantageous as it minimizes excess water added to the acid soaking process. Without recycling the pressate/filtrate within one or more stages, make-up water may need to be added in order to achieve the desired consistencies and/or pH values. However, in practice the amount of water within the acid soaking system is limited in order to avoid excessive pumping and/or cation exchange costs (e.g., the acid soaking process has a minimum practical level of solids consistency). In the absence of pressate/filtrate recycling, make-up water added to the acid soaking process can necessitate 1) purging a portion of the mineralized soaking liquid, which results in a loss of sulfuric acid, or 2) evaporating at least a portion of the mineralized soaking liquid upstream of cation exchange, either of which has significant operating and capital cost.

Recycling less than 50% of the pressate/filtrate within a stage (i.e., a pressate recycle fraction of less than 50%) can be advantageous for stages where the pressate/filtrate has a relatively high mineral concentration (e.g., for early stages and/or when the pressate/filtrate is fed directly to cation exchange). Recycling more than 50% of the pressate/filtrate within a stage (i.e., a pressate recycle fraction of more than 50%) can be advantageous for latter stages and/or where the pH of the pressate/filtrate is relatively low. In one embodiment, the pressate recycle fraction for the multi-stage, countercurrent acid soak increases with increasing stage number. Appropriate selection of the conditions will be apparent to those skilled in the art having the benefit of the teachings herein.

In one embodiment, the acid soaking process is a multi-stage, countercurrent acid soak, wherein one or more stages receives clean sulfuric acid solution from cation exchange. In one embodiment, the clean sulfuric acid solution is distributed to the different stages according to stage number, wherein earlier stages receive a higher fraction of the clean sulfuric acid solution. Providing most of the clean sulfuric acid solution to earlier stages (e.g., the first stage) of the acid soaking process is advantageous as most of the minerals can dissolve in these stages and/or the pressate recycle fraction can be lower. In one embodiment, less than about 50%, less than about 40%, less than about 30%, less than about 20%, or less than about 10% of the clean sulfuric acid produced by cation exchange is provided to the final stage of the acid soaking process, by weight.

In one embodiment, the acid soaking process is a multi-stage, countercurrent acid soak, wherein one or more stages receive make-up sulfuric acid solution (e.g., fresh acid). In one embodiment, the fresh sulfuric acid solution is concentrated sulfuric acid or a sulfuric acid solution that is between about 5% to about 10%, by weight, sulfuric acid in water. In one embodiment, the make-up sulfuric acid solution is distributed only to one stage (e.g., the first stage or the final stage). Providing the make-up sulfuric acid solution only to the final stage is particularly advantageous. In one embodiment, more than about 50%, more than about 60%, more than about 70%, more than about 80%, or more than about 90% of the make-up sulfuric acid is provided to the final stage of the acid soaking process, by weight.

In general, the conditions for the acid soaking process can be selected to remove a desired amount of minerals (e.g., more than 50% of the calcium and/or more than 50% of the magnesium) from the feedstock, and/or to provide a desired pH and/or consistency of the demineralized feedstock fed to pretreatment. These conditions include a) the number of stages, b) whether it is co-current and/or countercurrent, c) the pH, temperature, duration, extent of mixing, and/or consistency in each soaking step, and d) the consistency provided in each solids/liquid separation. For example, more minerals typically can be dissolved with increasing temperature, decreasing pH, and/or decreasing consistency (to some extent) in the acid soak step.

The pH and/or consistency in each acid soak step can be dependent on the flow rate of overflow (e.g., related to the pressate recycle fraction and efficiency of the solids/liquid separation) and/or the source and amount of clean and/or make-up sulfuric acid added. As will be understood by those skilled in the art, for a given pH, the pressate recycle fraction and/or the amount of fresh and/or make-up acid added to each stage can be determined from mass balance and acid-base calculations. Mass balance calculations are known in the art and are commonly used in multi-stage countercurrent contacting processes (e.g., extractions). Acid-base calculations determine the relationship between acid concentration and cation concentration and are familiar to those skilled in the art. Appropriate selection of the conditions will be further apparent to those skilled in the art having the benefit of the teachings herein. For example, FIG. 2b shows some effective conditions for the embodiment in FIG. 2a.

Figure 2B:
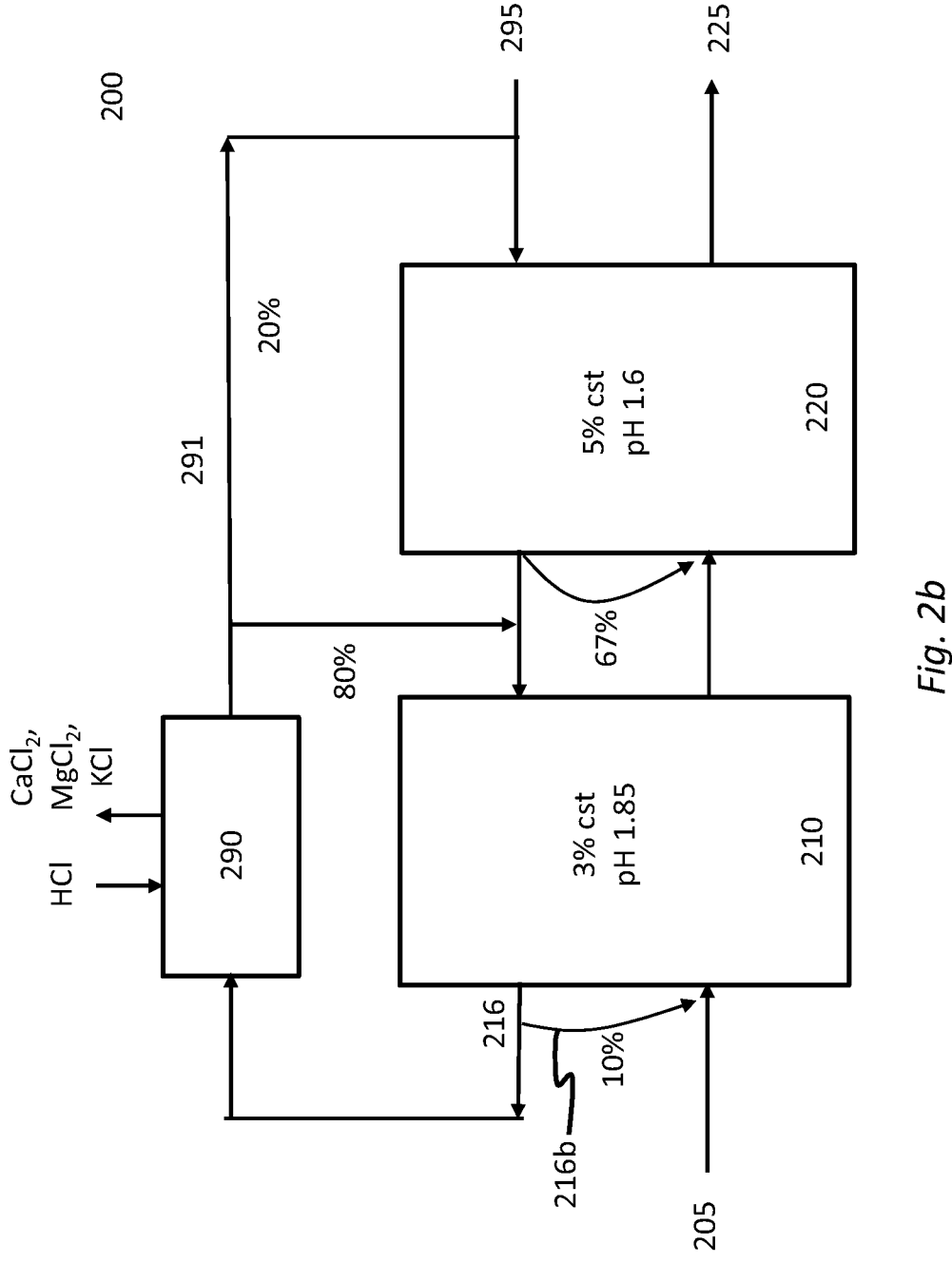
FIG. 2*b* is a schematic diagram illustrating some conditions of the two-stage acid soak, according to one embodiment.

Referring to FIG. 2b, the acid soaking step in the first stage 210 is conducted at a pH of about 1.85 and a consistency (cst) of about 3%, whereas the acid soaking step in the second stage 220 is conducted at a pH of about 1.6 and a consistency of about 5%. The clean sulfuric acid solution 291 produced from cation exchange is distributed between the first stage (e.g., about 80%) and the second stage (e.g., about 20%), by weight. In addition to the clean sulfuric acid solution 291 provided to each stage 210, 220 and the make-up sulfuric acid 295 added to the second stage 220, part of the mineralized soaking liquid (e.g., pressate) provided by the solids/liquid separation in each stage is reused directly for soaking in the respective stage (i.e., part 216b of the pressate 216 is recycled within the first stage 210). In FIG. 2b, the pressate recycle fraction for the first stage is 10%, while the pressate recycle fraction for the second stage is 67%.

Advantageously, the acid soaking step in the second stage 220 is conducted at pH 1.6, which is close to the pH used in the downstream pretreatment. Accordingly, the second acid soak stage 220 increases the percentage of minerals removed and reduces the amount of acid that needs to be added downstream of the acid soaking process 200 (i.e., for pretreatment). For example, if the pretreatment is conducted at a pH of 1.6 no additional sulfuric acid is required.

Figure 3:
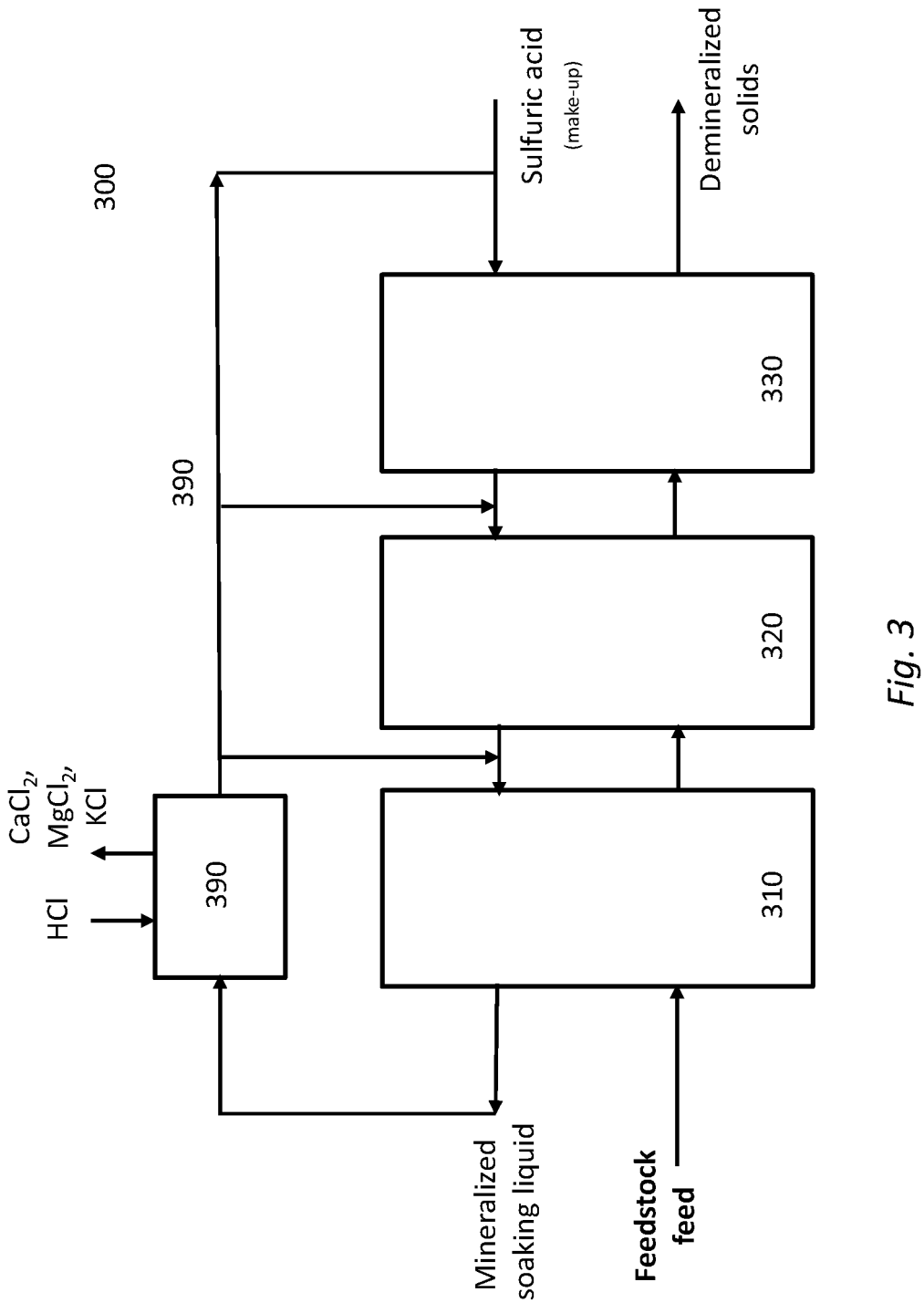
FIG. 3 is a flow diagram illustrating an embodiment of a three-stage acid soak.

Referring to FIG. 3, there is shown a schematic diagram of a multi-stage sulfuric acid soaking process in accordance with one embodiment. In this embodiment, the acid soaking process is a three-stage soaking process 300 that includes a first stage 310, a second stage 320, and a third stage 330, wherein clean sulfuric acid solution produced from cation exchange 390 is distributed between the first stage 310, the second stage 320, and/or the third stage 330. Like the embodiment illustrated in FIGS. 2a and 2b, this embodiment is a multi-stage countercurrent acid soak wherein the solids (e.g., which can be referred to as underflow) generally move from left to right (i.e., move downstream) and the soaking liquid (e.g., which can be referred to as overflow) generally moves from right to left (i.e., moves upstream). In such multi-stage countercurrent systems, the liquid (overflow) between stages is substantially solid free, while some liquid is retained in the solids (underflow). As the solids (underflow) progress through each successive stage, more minerals can be dissolved from the feedstock and the mineralized soaking liquid retained with the solids is increasingly diluted (i.e., has a lower mineral concentration). Accordingly, for multi-stage countercurrent acid soaks, the final underflow (i.e., demineralized feedstock from final stage) can be wet with substantially clean/fresh sulfuric acid solution, whereas the final overflow (i.e., mineralized soaking liquid) can contain substantially all of the dissolved minerals. In one embodiment, the acid soaking process is a 2-stage countercurrent acid soak. In one embodiment, the acid soaking process is a 3-stage countercurrent acid soak.

In one embodiment, the conditions for the acid soaking process are selected such that at least 50%, at least 60%, at least 70%, at least 75%, at least 80%, or at least 90% of the calcium originally present in the lignocellulosic feedstock is removed by the acid soaking process. In one embodiment, the conditions for the acid soaking process are selected such that at least 50%, at least 60%, at least 70%, at least 75%, at least 80%, or at least 90% of the magnesium originally present in the lignocellulosic feedstock is removed by the acid soaking process. In one embodiment, the conditions for the acid soaking process are selected such that at least 50%, at least 60%, at least 70%, at least 75%, at least 80%, or at least 90% of the potassium originally present in the lignocellulosic feedstock is removed by the acid soaking process. In one embodiment, the conditions for the acid soaking process are selected such that at least 50%, at least 60%, at least 70%, at least 75%, at least 80%, or at least 90% of the minerals originally present in the lignocellulosic feedstock are removed by the end of the acid soaking process. In one embodiment, the conditions for the acid soaking process are selected such that at least 50%, at least 60%, at least 70%, at least 75%, or at least 80% of the ash originally present in the lignocellulosic feedstock is removed by the end of the acid soaking process.

While the acid soaking process disclosed herein can remove all or most of the water soluble potassium and/or sodium originally present in the lignocellulosic feedstock, and a large part of the calcium and/or magnesium (i.e., which are not readily removed with water alone), it can be advantageous to provide a water wash upstream of the acid soaking process in order to remove water soluble cations such as sodium and/or potassium prior to the acid soaking process. For example, lignocellulosic feedstock often contains about 0.2% to about 4% (w/w) potassium, which can be largely removed by one or more water washing stages. It can be advantageous to remove these minerals prior to the acid soaking process because the wash liquor, which can contain potassium and/or sodium (e.g., as carbonate salts), is useful as a source of alkali for the process (e.g., to adjust the pH of the pretreated material). In addition, removing the potassium and sodium in the water wash decreases the amount of sulfuric acid consumed in the acid soak and pretreatment.

In one embodiment, the demineralization includes a washing process upstream of the acid soaking process. In one embodiment, the washing process includes one or more washing stages, wherein each washing stage includes:

(a) contacting the feedstock with wash water, and (b) a solids/liquid separation wherein the feedstock is separated from at least a portion of the wash water.

In general, the wash water is water or an aqueous solution having a pH between about 3 and 9.5. In one embodiment, the incoming wash water is primarily fresh water and/or contains fresh water. In one embodiment, the incoming wash water contains process water (i.e., water or an aqueous stream obtained from the process), which is provided after a partial purification, full purification, or without significant purification. For example, in one embodiment, the incoming wash water contains flash condensate. In one embodiment, the incoming wash water contains water from an evaporation. In one embodiment, the incoming wash water contains treated effluent from the anerobic digester (e.g., after the minerals are removed from the effluent using cation exchange). In one embodiment, the incoming wash water is an aqueous solution having a pH between about 3 and about 9, between about 4 and about 8, between about 4.5 and about 8, or between about 5 and about 7.5. The pH in each of the one or more washing stages can be higher than the pH of the incoming wash water as the pH increases as minerals are dissolved. In one embodiment, the incoming wash water is free of added acid. Providing an incoming wash water that is close to neutral and/or free of added acid is advantageous when the wash liquor is used for pH adjustment within the process (e.g., as-is or after being concentrated), however, if the incoming wash water is obtained from cation exchange of the effluent of the anaerobic digester, the pH may be lower. The term "incoming wash water", as used herein, refers to one or more streams that are provided to the washing process for one or more stages of the washing process. When the washing process includes more than one wash stage, the different stages may have the same or different conditions.

The conditions for each stage of the washing process can be any suitable conditions that remove a sufficient amount of water-soluble minerals such as potassium and/or sodium (e.g., total of all washing stages) from the lignocellulosic feedstock. In one embodiment, at least 50%, at least 60%, at least 70%, at least 75%, at least 85%, at least 90%, or substantially all of the potassium present in the lignocellulosic feedstock is removed in the washing process. In one embodiment, between about 50% and about 100% of the potassium and sodium from the lignocellulosic feedstock is removed in the washing process. In one embodiment, between about 75% and about 100% of the potassium and sodium from the lignocellulosic feedstock is removed in the washing process.

The washing process typically does not hydrolyze hemicellulose or cellulose in a significant amount (e.g., less than 5%) and does not remove a sufficient amount of calcium and/or magnesium (i.e., an appreciable amount of calcium and/or magnesium is removed in the acid soaking process). In one embodiment, less than about less than about 25%, less than about 20%, less than about 15%, less than about 10%, or less than about 5% of the calcium is removed in the washing process (i.e., that is conducted upstream of the acid soaking process).

Some non-limiting examples of conditions for the washing process that can be selected to improve the washing process include: the number of stages; whether it is co-current and/or countercurrent; the temperature, duration, and the consistency or water/feedstock ratio in each washing step; and the consistency provided in each solids/liquid separation.

In one embodiment, the number of stages, temperature of the wash water, water/feedstock ratio and the duration of each washing step, is selected to dissolve a sufficient amount of water soluble minerals such as potassium and/or sodium (e.g., total of all washing stages). In one embodiment, the washing process is a multi-stage washing process having 2, 3, or more stages. In one embodiment, the temperature of the wash water in each stage is between about 10° C. and about 95° C., between about 20° C. and about 90° C., between about 30° C. and about 90° C., between about 25° C. and about 85° C., between about 30° C. and about 80° C., between about 40° C. and about 90° C., between about 40° C. and about 80° C., or between about 50° C. and about 80° C. In one embodiment, the contact time in each washing stage is at least about 1 minute, at least about 2 minutes, at least about 3 minutes, at least about 4 minutes, or at least about 5 minutes. In one embodiment, the contact time in each washing stage is between about 1 minute and about 5, 10, 15, 20, 25, 30, 35, 40, or 45 minutes. In one embodiment, the water to feedstock ratio (water/feedstock) is between about 2/1 and about 25/1, or any value therebetween, including for example, at least 2.5/1, at least 3/1, at least 4/1, at least 5/1, at least 6/1, at least 7/1, at least 8/1, at least 9/1, at least 10/1, at least 15/1, or at least 20/1. The water to feedstock ratio refers to the weight of the overflow (e.g., wash water) per unit weight of the underflow (i.e., dry solids).

In general, increasing the water/feedstock ratio, increasing the number of stages, increasing the temperature, and increasing the contact time, can increase the potassium dissolution. Providing a multi-stage water wash, wherein in each stage the wash water temperature is between about 40° C. and about 80° C., the total contact time is between about 10 minutes and about 30 minutes, the water/feedstock ratio is between about 2/1 and about 9/1 can effectively dissolve potassium from lignocellulosic feedstock prior to an acid soak (e.g., remove more than 90% of the potassium from wheat straw). Varying the number of stages can have a significant effect on the potassium dissolution. For example, consider a washing process wherein each stage uses water at 50° C., has water/feedstock ratio of 5.4/1, and a residence time (contact time) of 30 minutes. In this case, a single stage removes only about 50% of the potassium, two stages removes about 80% of the potassium, and three stages can remove about 90% of the potassium. In one embodiment, the washing conditions are selected to remove at least 70%, at least 80%, or at least 90% of the potassium originally present in the feedstock. For example, 90% of the potassium can be removed from wheat straw when the water/feedstock ratio is about 9 to 1 and the total contact time is about 20 minutes, or when the water/feedstock ratio is about 5 to 1 and the total contact time is 45 minutes.

In general, the washing process can be conducted using the same type of equipment used for the acid soaking process and/or any commercial washing/leaching equipment commonly used in the pulp and paper industry (e.g., batch, semi-continuous, or continuous, agitated or non-agitated, co-current or counter current). For example, the washing process may include spraying the feedstock with the wash water, immersing the feedstock in the wash water, and/or passing the feedstock through a tank containing the wash water. In one embodiment, the washing process includes at least one step wherein the feedstock is soaked with wash water at a consistency between about 2% and 12%. Some examples of washing equipment include, but are not limited to, agitated vats, continuous stirred vessel, washing drums, and pulpers. For example, a twin turbo washer may provide suitable residence time, agitation, and consistency.

In one embodiment, the washing process is combined with and/or includes size reduction of the lignocellulosic feedstock. For example, in one embodiment one or more washing steps is conducted with a hydropulper. In one embodiment, the washing process includes washing the lignocellulosic feedstock, and pressing the wet feedstock through one roll press or a series of roll presses to remove at least a portion of the wash water and soluble minerals from the feedstock and to shear the feedstock to produce feedstock particles having a reduced size. In one embodiment, the washing process uses one or more roll presses as described in U.S. Pat. No. 7,709,042.

In one embodiment, the washing process uses equipment that provides both washing and solids/liquid separation (e.g., an inclined screw with washing). In one embodiment, the washing process is conducted in a counter current washing system that uses immersion or percolation technologies.

In one embodiment, the washing process produces a washed feedstock (e.g., wet cake) having a consistency between about 15% and about 40%, or between about 20% and 30%, which is fed to the acid soaking process. In one embodiment, the washed feedstock contains less than 50%, less than 40%, less than 30%, less than 20%, or less than 10% of the potassium originally present in the lignocellulosic feedstock.

In general, the washing process produces a wash liquor that has a relatively high potassium and/or sodium concentration. In one embodiment, this wash liquor is recycled within the process. For example, in one embodiment, the wash liquor is used to adjust pH within the process. In one embodiment, the wash liquor is used to adjust the pH of the pretreated slurry, or a part thereof (e.g., the liquid part). In these embodiments, the wash liquor can be used directly (i.e., as-is) or can be concentrated (e.g., by evaporation or reverse osmosis) prior to being recycled within the process. In embodiments where the wash liquor is recycled in the process (e.g., for pH adjustment), the wash liquor can be treated to remove sand. In one embodiment, the wash liquor is fed to the anaerobic digester (e.g., for diluting the contents of the anaerobic digester, for increasing the pH of the contents of the anerobic digester, and/or for wastewater treatment). In one embodiment, the wash liquor is used to adjust the pH of a secondary stream fed to the anaerobic digester. In one embodiment, the wash liquor is fed to the wastewater treatment.

Providing a multi-stage countercurrent wash is particularly advantageous as it can remove more sodium and/or potassium from the feedstock, can provide a wash liquor that has a higher concentration of sodium and/or potassium (i.e., without further concentration), and/or can reduce the amount of water used in the process. For example, as discussed above, a three stage countercurrent wash can remove about 90% or more of the potassium from the feedstock, and can, for at least wheat straw, provide a wash liquor having sufficient potassium to increase the pH of the pretreated material (e.g., solids and/or liquid), or at least significantly reduce the amount of alkali (e.g., sodium hydroxide, ammonia, or lime) that is used for the same.

A demineralization process that includes both a washing process and a subsequent acid soaking process is particularly advantageous. In particular, the washing process can remove an appreciable amount of potassium and/or sodium from the lignocellulosic feedstock, thereby reducing the amount of sulfuric acid required to neutralize the minerals present in the lignocellulosic feedstock during the acid soaking process. This can increase the efficiency of the acid soaking and/or cation exchange processes.

Advantageously, the washing process can remove an appreciable amount of the minerals present as salts of monovalent cations (e.g., sodium and/or potassium), while the acid soaking process can remove an appreciable amount of the minerals present as salts of divalent cations (e.g., calcium and/or magnesium). Other minerals that may be present in the lignocellulosic feedstock (e.g., iron (Fe) and/or aluminum (Al)) can also be removed in the acid soaking process. Substantially removing the mono-valent and di-valent minerals in different processes may be advantageous in terms of the disposal of and/or recycling of the minerals.

The removal of an appreciable amount of minerals such as calcium and/or magnesium upstream of pretreatment has the potential to improve the pretreatment (e.g., reduce residual xylan, which can increase xylose yield and/or improve hydrolysis), allow a higher pretreatment pH while still providing an effective pretreatment, prevent mineral build up in the pretreatment reactor, and/or improve anerobic digestion. For example, while it is generally advantageous to use less acid and still be able to achieve the low pH values associated with an effective pretreatment, it has been found that the demineralization step described herein can remove a sufficient amount of minerals from the lignocellulosic feedstock that the pretreatment can be effective at higher pH values (e.g., between 1.4 and 1.8).

In one embodiment, the amount of potassium removed in the washing process is at least at least 70%, at least 75%, at least 80%, at least 85%, at least 90%, or at least 95% of the potassium originally present in the lignocellulosic feedstock, and the amount of calcium and/or magnesium removed in the acid soaking process is sufficiently high that at least 80%, 85%, or 90% of the minerals originally present in the lignocellulosic feedstock are removed. The amount of mineral that is removed by the demineralization process can be determined by measuring the concentration of each of the minerals in the untreated feedstock (e.g., expressed as mg mineral/kg of dry feedstock) and the concentration of each of the minerals in the demineralized feedstock. The amount of each mineral is the feedstock is determined with ICP-OES.

In one embodiment, sufficient minerals are removed from the lignocellulosic feedstock that the amount of sulfuric acid added is less than about 17 kg $H_2SO_4$/ton of dry lignocellulosic biomass, less than about 16 kg $H_2SO_4$/ton of dry lignocellulosic biomass, or less than about 15 kg $H_2SO_4$/ton of dry lignocellulosic biomass, less than about 14 kg $H_2SO_4$/ton of dry lignocellulosic biomass, less than about 12 kg $H_2SO_4$/ton of dry lignocellulosic biomass, less than about 11 kg $H_2SO_4$/ton of dry lignocellulosic biomass, less than about 10 kg $H_2SO_4$/ton of dry lignocellulosic biomass, less than about 9 kg $H_2SO_4$/ton of dry lignocellulosic biomass, less than about 8 kg $H_2SO_4$/ton of dry lignocellulosic biomass, less than about 7 kg $H_2SO_4$/ton of dry lignocellulosic biomass, less than about 6 kg $H_2SO_4$/ton of dry lignocellulosic biomass, or less than about 5 kg $H_2SO_4$/ton of dry lignocellulosic biomass. Providing less than about 12 kg $H_2SO_4$/ton of dry lignocellulosic biomass for pretreatment can be particularly advantageous for the downstream anerobic digestion.

Sulfuric Acid Pretreatment

Pretreatment refers to one or more steps wherein the lignocellulosic feedstock is treated such that the fiber structure thereof is disrupted and the cellulose in the lignocellulosic biomass is made more susceptible and/or accessible to enzymes in a subsequent hydrolysis. The pretreatment typically converts the hemicellulose, or a part thereof, to sugars (e.g., xylose, arabinose, mannose, and/or galactose) and/or oligomers, and may convert part of the cellulose to glucose.

Sulfuric acid pretreatments are known in the art and the conditions (e.g., pH, temperature, and time) are typically selected to carry out almost complete hydrolysis of the hemicellulose (e.g., to sugars and/or oligomers), with minimal conversion of cellulose (e.g., to glucose). In one embodiment, the pretreatment is conducted such that the amount of xylan hydrolyzed to xylose is greater than about 50 wt %, about 60 wt %, about 70 wt %, about 80 wt %, or about 90 wt %. The amount of xylan hydrolyzed is determined using a carbohydrate assay (i.e., based on Determination of Structural Carbohydrates and Lignin in Biomass-LAP (Technical Report NREL/TP-510-42618)).

Dilute sulfuric acid pretreatment is generally preferred over concentrated acid pretreatments for ethanol production. Dilute sulfuric acid pretreatment conditions for lignocellulosic feedstocks typically include a pretreatment temperature in the range of about 150° C. to about 260° C., or any amount therebetween, for example about 160° C., about 170° C., about 180° C., about 190° C., about 200° C., about 210° C., or about 220° C., about 230° C., or about 240° C., for a time period of about 0.1 to about 30 minutes, or any amount therebetween, including about 1 minute, about 3 minutes, about 5 minutes, about 8 minutes, about 10 minutes, about 12 minutes, or about 15 minutes, and at a pH of about 0.8 to about 2.5, or any amount therebetween, for example a pH of about 1, about 1.2, about 1.4, about 1.6, or about 1.8. The combination of time, temperature, and pH may be any suitable conditions known in the art. In a non-limiting example, the temperature, time and pH may be as described in U.S. Pat. No. 4,461,648. Those skilled in the art will understand that the temperature can vary within a range during the pretreatment.

In general, dilute sulfuric acid pretreatment can be conducted in continuous mode or batch mode, in any suitable reactor or system, as known in the art. For example, some non-limiting examples of pretreatment reactors include batch reactors, screw conveyers, and steam guns. In order to accommodate the relatively high temperatures (e.g., greater than 150° C.) and relatively short pretreatment times (e.g., under 30 minutes), the pretreatment reactor and/or pretreatment system is typically pressurizable and includes one or more inlets for providing steam (e.g., saturated steam at a pressure of between about 50 psig to about 700 psig or any amount therebetween, for example 100 psig, 150 psig, 200 psig, 250 psig, 300 psig, 350 psig, 400 psig, 450 psig, 500 psig, 550 psig, 600 psig, 650 psig, or 700 psig, or any amount therebetween). Pretreatment systems are known, and may for example, include a heating device upstream of the pretreatment reactor (see, e.g., US20130071903). Pretreatment reactors and/or pretreatment systems often include a discharge valve (e.g., blow-valve). When lignocellulosic feedstock is heated to a high temperature (e.g., greater than 160° C.), followed by a sudden pressure drop as it is discharged through a blow valve into a flash tank, it undergoes an explosive decompression. This flashing cools the pretreated material. Optionally, flashing is achieved using a multiple flash tanks. The pretreated material from such "steam explosion" pretreatments can be more uniform.

The sulfuric acid used in pretreatment is provided in an amount sufficient to provide the desired pH. In one embodiment, sufficient sulfuric acid is added to provide a pH less than about 2, less than about 1.8, less than about 1.6, less than about 1.4, or less than about 1.2. In one embodiment, sufficient sulfuric acid is added to provide a pH in the range between about 0.8 and 2.5, between about 1 and about 2.5, between about 1.1 and about 2, between about 1.2 and about 1.8, between about 1.3 and about 1.6, or between about 1.4 and about 1.7. Advantageously, removing an appreciable amount of minerals from the feedstock can improve the pretreatment when the pH is above 1.4 (e.g., 1.5, 1.6, 1.7, 1.8, or any value therebetween).

The sulfuric acid used in pretreatment can be injected into the pretreatment reactor and/or upstream of the pretreatment reactor. In one embodiment, all of the sulfuric acid used in pretreatment is provided in the demineralized feedstock produced from the demineralization process. In one embodiment, sufficient sulfuric acid is mixed with the demineralized feedstock to reduce the pH thereof to the desired level (e.g., a pH between 1 and about 1.8). In one embodiment, the supplemental sulfuric acid is mixed with the demineralized feedstock in a heating device upstream of the pretreatment reactor and/or in the pretreatment reactor. In one embodiment, the supplemental sulfuric acid is mixed with the demineralized feedstock as part of the solids/liquid separation of the final stage of the acid soak stage (e.g., in the screw press).

As will be understood by a person of skill in the art, the pretreatment time and/or temperature will depend on the temperature and acid concentration in the pretreatment reactor. In one embodiment, the pH is between 1 and 1.9, the pretreatment time is between 1 and 15 minutes, and the pretreatment temperature is between 160° C. and 210° C.

When the one or more flash tanks includes an atmospheric flash tank, the pretreated material can be cooled to about 100° C. or lower. The pretreated material typically has a reduced solids consistency relative to that entering pretreatment.

First Conversion Process

In general, at least part of the pretreated material is converted to a chemical and/or fuel in a first bioconversion process that includes an enzymatic hydrolysis and a fermentation. As the pretreated material typically is relatively hot (e.g., about 100° C.) and at a low pH (e.g., less than about 2.5) after it is discharged from the pretreatment system, it can be conditioned (e.g., cooled, pH adjusted, and/or diluted) for downstream enzymatic hydrolysis and/or fermentation. For example, the temperature of the pretreated material can be adjusted using any suitable method known in the art, for example, but not wishing to be limiting, by using cool water directly or a cooling jacket. The pH of the pretreated material can be adjusted by adding alkali (e.g., sodium hydroxide, lime, ammonia). In one embodiment, the conditioning includes adding at least part of the wash liquor produced during the demineralization process.

The pretreated material discharged from pretreatment is a slurry containing undissolved solids and liquids. The liquid is an aqueous solution that contains sugars produced during pretreatment (e.g., xylose, glucose, arabinose, mannose, and/or galactose) and sulfuric acid. The undissolved solids include cellulose and typically include lignin. In general, the solids and liquids of the pretreated material can be treated together and/or separately.

In one embodiment, the pretreated material discharged from pretreatment is subjected to a solids/liquid separation that produces a liquid stream and a solids stream. In one embodiment, the solids stream is fed to enzymatic hydrolysis without the liquid stream. In this embodiment, the solids stream may be washed prior to enzymatic hydrolysis (e.g., which can cool, adjust the pH of, and/or dilute the solids prior to enzymatic hydrolysis), or may not be washed prior to enzymatic hydrolysis (i.e., are unwashed solids). In one embodiment, at least part of the liquid stream from the solids/liquid separation is fed to enzymatic hydrolysis with the solids stream. In one embodiment, at least part of the liquid stream is conditioned and fed to fermentation (i.e., where it can be fermented separately or together with glucose produced by the enzymatic hydrolysis). In one embodiment, the part of the liquid stream conditioned and fed to fermentation is fermented separately from the glucose produce by enzymatic hydrolysis using a fermentation organism selected to be effective at converting xylose and/or other pentoses to the desired fermentation product. In one embodiment, at least part of the liquid stream is fed to anaerobic digestion. In this embodiment, alkali (e.g., from the wash liquor) may be added to the liquid stream to adjust the pH of the liquid stream such that it is compatible with the bacteria in the anaerobic digestor.

In one embodiment, the pretreated material discharged from pretreatment is not subjected to a solids/liquid separation, and the whole slurry (liquids and solids) is fed to enzymatic hydrolysis. In this embodiment, the whole slurry is conditioned for enzymatic hydrolysis (e.g., cooled pH adjusted, and/or diluted). Feeding the whole pretreated slurry to enzymatic hydrolysis is advantageous in terms of reducing sugar loss and/or reducing water consumption. In one embodiment, the pretreated material discharged from pretreatment is subjected to a solids/liquid separation, the solids stream is fed to enzymatic hydrolysis without washing, and a slurry/solution containing the glucose produced from enzymatic hydrolysis is combined with the liquid stream from the solids/liquid separation (e.g., after the liquid stream is conditioned) for a co-fermentation of the xylose and glucose. In addition to preventing sugar loss and/or reducing water consumption, this embodiment can require less enzyme in the enzymatic hydrolysis (i.e., than required for hydrolysis of the whole slurry). In this embodiment, the wash liquor, or a part thereof, can be used to condition the solids and/or liquids from the solids/liquid separation.

As familiar to those skilled in the art, enzymatic hydrolysis is carried out using cellulase enzymes, with the pH and temperature of the hydrolysis slurry selected so as to be compatible with the enzymes. Cellulase enzymes are well known. The terms "cellulase enzyme", "cellulase", or "enzyme", as used herein, refers to an enzyme or multienzyme mixture that can break cellulose chains into products such as glucose, cellobiose, and other cellooligosaccharides. For example, cellulase can refer to any of several enzymes produced by fungi, bacteria, or protozoans that catalyze cellulolysis. Cellulase enzyme, may for example, include exo-cellobiohydrolases (CBH), endoglucanases (EG) and β-glucosidases (BG) that can be produced by a number of plants and microorganisms. In addition to CBH, EG and BG, cellulase can include accessory enzymes that may aid in the enzymatic digestion of cellulose (e.g., glycoside hydrolase 61 (GH61), swollenin, expansin, lucinen and cellulose-induced protein (Cip).) As will be understood by those skilled in the art, enzyme dose may depend on the activity of the enzyme at the selected pH and temperature and/or the hydrolysis time. In one embodiment, cellulase is added at a dosage between about 2 to 20 mg protein per gram cellulose, between about 2 to 15 mg protein per gram cellulose, or between about 2 to 12 mg protein per gram cellulose. The protein is quantified using either the bicinchoninic acid (BCA) assay or the Bradford assay. In one embodiment, the hydrolysis is conducted at or near the temperature and/or pH optimum of the enzyme(s). For example, cellulase enzymes may have optimum pH values between about 3 and about 7 (e.g., often between about 4.5 and about 5.5) and a temperature optimum between about 40° C. and about 60° C. (e.g., often between about 45° C. to 55° C.). In one embodiment, enzymatic hydrolysis is conducted at a consistency between about 4% to about 20%, between about 6% and 18%, or between about 8% and 15%. In one embodiment, the enzyme dosage and hydrolysis time are selected to achieve a sufficiently high level of cellulose conversion (e.g., greater than about 75%, greater than about 80%, or greater than about 85%). In one embodiment, the hydrolysis is continued for at least 12 hours. In one embodiment, the hydrolysis is continued for about 24 to about 250 hours, or any amount of time therebetween.

Enzymatic hydrolysis produces an aqueous slurry that contains glucose in addition to any unconverted cellulose and other unconverted, suspended solids (e.g., lignin). If the enzymatic hydrolysis is conducted on the whole pretreated slurry (i.e., solids and liquids of the pretreated material) the slurry produced by enzymatic hydrolysis can also contain the sugars produced from pretreatment (e.g., xylose) and any sulfate produced by neutralizing sulfuric acid provided for pretreatment.

As familiar to those skilled in the art, the sugar(s) produced from pretreatment and/or enzymatic hydrolysis can be converted to a fermentation product (e.g., ethanol, butanol, xylitol, acetic acid, lactic acid, succinic acid, etc.) in one or more fermentations that use a suitable microorganism (e.g., yeast or bacteria). Microorganisms for producing fermentation products from sugars are well-known and can be selected in dependence upon the sugars present and the desired fermentation product. For example, glucose and/or other hexoses are often fermented to ethanol with *Saccharomyces* spp. yeast (e.g., a wild-type *Saccharomyces cerevisiae* or a genetically modified yeast), whereas xylose and/or arabinose can be fermented to ethanol using a yeast strain that naturally contains, or has been engineered to contain, the ability to ferment these sugars to ethanol. Alternatively, xylose and other pentose sugars may be fermented to xylitol by yeast strains selected from the group consisting of *Candida, Pichia, Pachysolen, Hansenula,*

*Debaryomyces, Kluyveromyces* and *Saccharomyces*. In one embodiment, the sugar(s) is converted to alcohol(s) using *Saccharomyces* spp. yeast. In one embodiment, the sugar(s) are converted to alcohol(s) using *Zymomonas* bacteria. As will be understood by those skilled in the art, fermentation typically includes providing nutrients for the growth of the fermentation microorganism (e.g., yeast extract, specific amino acids, phosphate, nitrogen sources, salts, trace elements and/or vitamins) and may include yeast recycle.

In general, each of the one or more fermentations is conducted at a pH and temperature selected to be compatible with the selected microorganisms. In one embodiment, the fermentation is performed at or near the temperature and/or pH optimum of the corresponding microorganism. For example, *Saccharomyces cerevisiae* typically has an optimum pH value between about 4 and about 5.5 and a temperature optimum between about 25° C. and about 35° C. *Zymomonas* bacteria typically have an optimum pH value between about 5 and about 6. The dose of the microorganism (s) will depend on various factors, including as the activity of the microorganism, the desired reaction time, the pH and the temperature. Fermentations for producing ethanol often have a reaction time between about 24 and 96 hours, although may be shorter or longer, and are conducted at a temperature between about 20° C. and about 40° C., although may be lower or higher. For example, thermophilic microorganisms are often used at higher temperatures. It should be appreciated that these parameters may be adjusted as desired by one of skill in the art to achieve optimal conditions.

As will be understood by those skilled in the art, the enzymatic hydrolysis and/or fermentation may be conducted as a separate hydrolysis and fermentation (SHF), a simultaneous saccharification and fermentation (SSF), or a hybrid hydrolysis and fermentation (HHF), using known techniques and equipment. For example, enzymatic hydrolysis can be conducted in one or more hydrolysis reactors, connected in series or in parallel, operated in continuous, fed-batch, or batch mode. In one embodiment, the hydrolysis is conducted in continuous mode in one or more continuous stirred vessel and/or one or more tubular reactors (e.g., PFRs), thereby providing greater productivity and lower costs. For a commercial-scale ethanol plant, the number of hydrolysis reactors may be, for example, between about 4 and about 12.

In general, the process includes a fermentation wherein glucose produced by enzymatic hydrolysis (and optionally the pretreatment) is fermented to a fermentation product (e.g., ethanol). In one embodiment, the glucose is obtained from the enzymatic hydrolysis of the whole pretreated slurry. In one embodiment, the glucose is obtained from the enzymatic hydrolysis of unwashed solids. In one embodiment, the glucose is obtained from the enzymatic hydrolysis of washed solids. In these embodiments, the fermentation produces a fermentation slurry/solution that contains the fermentation product (e.g., ethanol) and any unfermented sugar. If the slurry produced by enzymatic hydrolysis is not subjected to a solids/liquid separation prior to fermentation, the fermentation slurry can contain unconverted cellulose and other unconverted, suspended solids. When part of the liquid from the pretreated slurry is fed to enzymatic hydrolysis (e.g., when the enzymatic hydrolysis is conducted on whole or unwashed pretreated slurry) and/or to fermentation, the fermentation slurry/solution can also include sulfate (s). For example, such sulfates may be derived from the sulfuric acid used in pretreatment and/or acid soaking process (e.g., and alkali used in conditioning). In one embodiment, the fermentation includes a first fermentation of sugar provided from enzymatic hydrolysis and a second other fermentation of sugar produced by pretreatment.

In general, the fermentation product(s) produced from fermentation may be recovered using methods known in the art. For example, ethanol produced from fermentation may be recovered using a process wherein ethanol is concentrated and/or purified from the fermentation slurry/solution. Ethanol recovery is commonly conducted as a distillation, wherein one or more distillation columns are used to separate the ethanol from other components (e.g., water). The distillation, which can be operated in continuous or batch mode, produces concentrated ethanol and still bottoms. Depending on the process, the still bottoms can include unfermented sugar, unconverted cellulose, lignin, ethanol, and/or sulfate/sulfuric acid (e.g., from pretreatment). For example, sulfates present in the fermentation slurry/solution are typically carried downstream to distillation.

After distillation, any water remaining in the concentrated ethanol is typically removed using a molecular sieve resin, membrane extraction, or other methods known to those of skill in the art to increase the ethanol concentration beyond the 95% that is typically achieved by distillation (e.g., a vapour phase drying). The vapour may then be condensed and denatured.

Advantageously, this conversion process converts at least part of the pretreated material to a chemical and/or fuel (i.e., the fermentation product or a product derived from the fermentation product). In addition, this conversion process produces one or more secondary streams, which contain an appreciable amount of sulfate as a result of the sulfuric acid used in pretreatment. For example, some secondary streams that can be produced by the process and that can contain an appreciable amount of sulfate, include but are not limited to, still bottoms and the liquid stream resulting from a solids/liquid separation of the pretreated slurry.

In addition to containing sulfates, such secondary streams can also contain organic matter that can be converted to biogas in anaerobic digestion. In particular, these streams can contain part of the lignocellulosic biomass (e.g., some of the C5 sugars, some lignin, some unconverted cellulose, and/or some ethanol, etc.) that can be converted to a fuel (e.g., biogas).

Second Conversion Process

In general, at least part of the pretreated material is converted to a chemical and/or fuel in a second bioconversion process that includes the production of biogas. Biogas refers to the gas produced by the anaerobic digestion of organic material. Biogas, which is a mixture of gases, is largely made up of methane ($CH_4$) and carbon dioxide ($CO_2$). Biogas often contains water and may contain hydrogen sulfide (e.g., if sulfur is present during the anaerobic digestion). The term "anaerobic digestion", as used herein, encompasses any process for microbially digesting organic matter under low oxygen conditions, or in the absence of oxygen.

Anaerobic digestion, which is often used to treat organic matter in waste streams, is typically conducted in one or more anaerobic digesters (e.g., arranged in series and/or in parallel). Anaerobic digesters are known in the art, and typically include for example, a tank, or other contained volume, such as a covered lagoon, designed to facilitate the breakdown of organic material by microorganisms under anaerobic or low oxygen conditions. Anaerobic digesters can be designed and/or operated in a number of configurations including batch or continuous, mesophilic or thermophilic temperatures, and low, medium or high rates. The rate refers to the reduction (or digestion) of chemical oxygen demand (COD) per unit of volume to the unit. The anaerobic digester may be adapted for handling or concentrating microbes. For example, the digester may utilize membranes, packing, settling and recycling. The term "anaerobic digester", as used herein, can refer to plurality of fluidly connected digesters.

The production of biogas in the second conversion process includes anaerobic digestion of organic matter, wherein at least some of the organic matter is obtained from one or more secondary streams produced in the first conversion process. In general, any secondary stream produced by the first conversion that has a relatively high concentration of organic matter may be suitable.

In one embodiment, the secondary stream contains a still bottoms stream or a liquid fraction of a still bottoms stream. For example, when the first conversion process produces cellulosic ethanol, the still bottoms resulting from ethanol recovery can contain a number of organic compounds. Feeding this stream to the anaerobic digestion can both treat the still bottoms (e.g., for recycle within the process or for disposal) and can produce biogas. In other words, anaerobic digestion of the still bottoms can simultaneously provide wastewater treatment and increase the fraction of the ligno-cellulosic feedstock converted to fuel. In general, both the solids and liquid from the still bottoms can be fed to the anerobic digester, however, it can be advantageous to only feed the liquid. In one embodiment, the still bottoms is subjected to solids/liquid separation to produce a solids stream that is fed to a boiler (e.g., where it is combusted for generating heat and/or electricity), and a liquid stream, wherein at least part of the liquid stream is fed to the anaerobic digester.

In one embodiment, the secondary stream contains the liquid fraction of the pretreated material, or part thereof. Pretreatment typically converts at least part of the hemicellulose to sugars that are dissolved in the liquid fraction of the pretreated slurry. A large part of the dissolved hemicellulose is xylose, which can require specific microorganisms for fermentation. Feeding at least part of the liquid fraction of the pretreated slurry to anaerobic digestion to produce biogas, provides an alternative approach to convert the xylose and/or other pentoses to fuel (e.g., alternative to fermenting to ethanol). In one embodiment, the pretreated slurry is subjected to a solids/liquid separation and at least part of the liquid stream is fed to anaerobic digestion (e.g., after pH adjustment).

In addition to the one or more secondary streams, the feed to the anaerobic digester can include one or more other aqueous streams produced by the process (e.g., flash condensate, spent cleaning water, and/or rectifier effluent). In one embodiment, flash condensate is fed to the anaerobic digester. In one embodiment, the wash liquor from the washing process is fed to the anerobic digester (e.g., for treatment and/or for pH control).

In one embodiment, the anaerobic digester is part of a wastewater treatment system. In one embodiment, the wastewater treatment system includes an aerobic digester and/or a reverse osmosis system downstream of the anerobic digestion. In one embodiment, treated wastewater from the wastewater treatment is used within the process. In one embodiment, the treated wastewater from the anaerobic digestion is recycled within the process without further purification. In one embodiment, sodium and/or potassium from the treated wastewater from the anaerobic digestion is used in a pH adjustment step of the process (e.g., for adjusting the pH of the solids and/or liquid of the pretreated slurry).

In one embodiment, the effluent from the anaerobic digester or a stream derived therefrom (e.g., effluent of an aerobic digester downstream of the anaerobic digester) is heated and the heat-treated effluent is used for pH adjustment. For example, consider the case where the effluent of an anaerobic digester has a pH of about 7.5. In this case, the relatively large potassium concentration in the effluent can be largely present as potassium bicarbonate salt, which is a relatively weak base. As the decomposition of potassium bicarbonate generally occurs between about 100° C. and 120° C., heating the effluent (e.g., in an evaporation process) can convert the potassium bicarbonate ($KHCO_3$) to potassium carbonate ($K_2CO_3$), which is a stronger base, while also concentrating the potassium. Accordingly, the heat-treated effluent can be used to adjust the pH of one or more streams (e.g., of pretreated material) more effectively (e.g., with less potassium and/or with less water). In one embodiment, the wash liquor, or a stream derived therefrom, is heated and the heat-treated wash water is used for pH adjustment (e.g., of the pretreated solids and/or liquid).

In general, the second conversion process includes collecting the biogas produced by the anaerobic digestion. In one embodiment, the collected biogas (e.g., raw biogas) is provided as a fuel. For example, in one embodiment, the raw biogas is used to produce heat and/or electricity for the process. In one embodiment, the collected biogas (e.g., raw biogas) is at least partially purified. Biogas purification refers to a process wherein the biogas is treated to remove one or more non-methane components (e.g., $CO_2$, $H_2S$, $H_2O$, $N_2$, $NH_3$, $H_2$, $O_2$, VOCs). Biogas purification technologies are well known in the art, and a biogas purification process can include any one technology or combination of technologies. Some non-limiting examples of biogas purification technologies include scrubbing, pressure swing adsorption, membrane separation, and cryogenic separation. In one embodiment, the collected biogas is treated to remove between 20% and 100% by weight of the carbon dioxide from the raw biogas. In one embodiment, a sufficient amount of non-methane components are removed so as to produce renewable natural gas (RNG), which is substantially interchangeable with pipeline natural gas (e.g., may contain more 95% methane). In one embodiment, the collected biogas is used to produce a fuel. In one embodiment, the collected biogas is used to produce a transportation fuel (e.g., RNG). In this embodiment, the methane and/or carbon dioxide from the biogas can be converted to the transportation fuel. The production of fuels from methane is well known, and may for example, include converting the methane to the fuel directly or through a syngas intermediate. For example, syngas produced by reforming methane can be converted to methanol, to gasoline or diesel (e.g., in a Fischer Tropsch reaction), or to ethanol (e.g., in a gas fermentation).

Advantageously, the second conversion process produces biogas from organic material in the one or more secondary streams, and therefore can increase the fraction of the lignocellulosic feedstock converted to fuel. However, in addition to containing an appreciable amount of organic matter, these secondary streams can also have a significant sulfate concentration (e.g., in an amount proportional to the amount of sulfuric acid used in pretreatment). For example, if the pretreated material is not washed prior to enzymatic hydrolysis, then the sulfuric acid ($H_2SO_4$) used in pretreatment can result in relatively high levels of sulfate ($SO_4^{2-}$) in the pH adjusted pretreated material, which can be carried through to the still bottoms, where it is concentrated.

When the feed to anaerobic digestion contains sulfur (e.g., sulfates and/or sulfuric acid), the sulfur can be converted to hydrogen sulfide in the anaerobic digester. Such conversion may be carried out by sulfate-reducing bacteria present during the anaerobic digestion. While this is generally advantageous in terms of wastewater treatment, wherein it is desirable to reduce the amount of sulfate in the wastewater, the competition for available electron donors (e.g., hydrogen or acetate) between the sulfate-reducing bacteria (SRB) and the methane-producing bacteria (MPB) can reduce the methane yield.

As described herein, the demineralization process removes minerals from the lignocellulosic feedstock such that less sulfuric acid is required for an effective pretreatment and such that lower concentrations of sulfate are present in the secondary streams. Accordingly, the process can provide a higher yield of biogas, and thus a higher yield of fuel from the second conversion.

In one embodiment, the secondary stream has a sulfate concentration not more than about 5 g/L, not more than about 4.5 g/L, not more than about 3.5 g/L, not more than about 3 g/L, not more than about 2.5 g/L, or not more than about 2 g/L. In one embodiment, the feed to the anaerobic digester (e.g., which includes the secondary stream and may include other streams) has a sulfate concentration not more than about 5 g/L, not more than about 4.5 g/L, not more than about 3.5 g/L, not more than about 3 g/L, not more than about 2.5 g/L, or not more than about 2 g/L. The sulfate amount of sulfate in a sample, which can also be expressed in mg per litre, can be determined using methods well known in the art (e.g., turbidimetric).

In one embodiment, the secondary stream has a calcium concentration not more than about 5 g/L, not more than about 4.5 g/L, not more than about 3.5 g/L, not more than about 3 g/L, not more than about 2.5 g/L, or not more than about 2 g/L. In one embodiment, the feed to the anaerobic digester has a calcium concentration not more than about 5 g/L, not more than about 4.5 g/L, not more than about 3.5 g/L, not more than about 3 g/L, not more than about 2.5 g/L, or not more than about 2 g/L. While the maintenance of salt concentration can permit good microbial growth in the anaerobic digester, the addition of excess minerals (e.g., such as $Mg^{2+}$ and/or $Ca^{2+}$) can potentially inhibit biogas production.

In one embodiment, the secondary stream has a BCOD/sulfate ratio of at least 6:1, at least 7:1, at least 8:1, at least 9:1, or at least 10:1. In one embodiment, the feed to the anaerobic digester has a BCOD/sulfate ratio of at least 6:1, at least 7:1, at least 8:1, at least 9:1, or at least 10:1. Both COD and BOD are commonly used to measure the amount of organic compounds in wastewater. While COD measures the amount of organics in sample that can by oxidized by chemicals, BOD measures the amount of organics in the sample that can be oxidized by microorganisms. More specifically, BOD represents the amount of dissolved oxygen needed by aerobic organisms to break down organic material present in a given sample at certain temperature over a specific time period. BOD is commonly expressed in milligrams of oxygen consumed per litre of sample during 5 days of incubation at 20° C. BOD and the methods of determining the same are well known in the art. The biologically degraded COD (BCOD) is related to the BOD by BCOD=BOD/0.85. The BCOD/sulfate ratio, which can determine if anaerobic digestion will be inhibited by sulfate and/or suffer loss of methane yield, is the ratio of the BCOD and the amount of sulfate (e.g., in g/g).

Recycle of the Soaking Liquid

The mineralized soaking liquid provided from the demineralization process contains minerals dissolved and/or released from the lignocellulosic feedstock. For example, the mineralized soaking liquid can contain sulfate salts of calcium, magnesium, sodium, potassium, iron, and/or aluminum. This aqueous steam is subjected to a process that removes one or more minerals from the liquid. In general, any method that can remove electrolytes and is suitable for removing the minerals present in the feedstock can be used. In a preferred embodiment, the one or more minerals are removed using cation exchange.

Cation exchange, which is a form of ion exchange, is well known in the art. In cation exchange, when an aqueous solution containing cations (e.g., $Ca^{2+}$, $Mg^{2+}$, $N^+$, $K^+$) is passed over an appropriately selected resin, these cations can be exchanged for cations bound to the resin. Such resins can be polymeric resins (porous solids or gels), zeolites, clay, or humus, or any suitable material. Cation exchange is commonly conducted in columns (e.g., having a length/diameter of 5 to 10, about 1, or about 0.1 to 0.5), wherein the aqueous solution containing the electrolytes is fed into the top, passes through the resin, and is withdrawn at the other end. Alternatively, cation exchange can be conducted in another system (e.g., a Simulated Moving Bed (SMB) system). The operating conditions, including pressure and flow rates, are readily selected by those skilled in the art.

In general, cation exchange resins can be either weak or strong acid cation exchange resins. Strong acid cation exchange resins, may for example, contain a polymeric structure having a strong acid functional group (e.g., $R—SO_3H$), whereas weak acid cation exchange resin may, for example, contain polymeric structure comprising a weak acid functional group (e.g., R—COOH). In a particularly advantageous embodiment, the cation exchange used to produce clean sulfuric acid solution uses a strong acid cation exchange resin in the hydrogen form. For example, strong acid cation exchange resins include the Dowex™ resins from Dow Chemical and the Amberjet™ resin from Rohm and Haas.

As described herein, the mineralized soaking liquid produced from the demineralization process is fed to cation exchange. If the mineralized soaking liquid contains fines, as can be found in pressate, the mineralized soaking liquid can be first filtered or screened. In the cation exchange, the positively charged cations in the mineralized soaking liquid (e.g., $K^+$, $Ca^{2+}$ and/or $Mg^{2+}$) are exchanged for hydrogen ($H^+$) bound to the resin, thereby removing the minerals form the sulfuric acid solution and producing a clean sulfuric acid solution.

When the resin is exhausted, it is regenerated by feeding a strong acid such as hydrochloric acid (HCl) through the resin, thereby exchanging the bound cations (e.g., $K^+$, $Ca^{2+}$ and/or $Mg^{2+}$) for $H^+$, and producing chloride salts (e.g., potassium chloride, calcium chloride, and/or magnesium chloride). If the acid soaking process is preceded by a washing process wherein most of the potassium is removed, there will be minimal amounts of potassium chloride salt produced. The chloride salts may be disposed of.

Advantageously, incorporating cation exchange within the process reduces water usage, reduces sulfuric acid consumption, and provides a relatively clean sulfuric acid solution. Further advantageously, embodiments wherein the feedstock is washed with water prior to the acid soaking process, thereby removing an appreciable amount of potassium, can improve the recycle of the soaking liquid. For example, for feedstocks such as wheat straw, about half of the minerals present, by weight, can be potassium. Removing half of the minerals from the feedstock with a water wash prior to the acid soaking process, can significantly increase the running time before the resin is exhausted. This reduces operation costs, including the cost of regenerants and disposal costs. In addition, there may be additional advantages to substantially separating the mono-valent cations (e.g., $K^+$ and/or $Na^+$) from the divalent cations (e.g., $Ca^{2+}$ and/or $Mg^{2+}$) upstream of the cation exchange. For ion exchange to be efficient there must be a difference in affinity between the cation loaded on the resin and the cation(s) to be removed from solution. Removing the mono-valent cations (e.g., $K^+$ and/or $Na^+$) upstream of the cation exchange can prevent the resin from being exhausted with monovalent cations, which may reduce the efficiency of divalent cation removal.

Figure 4:
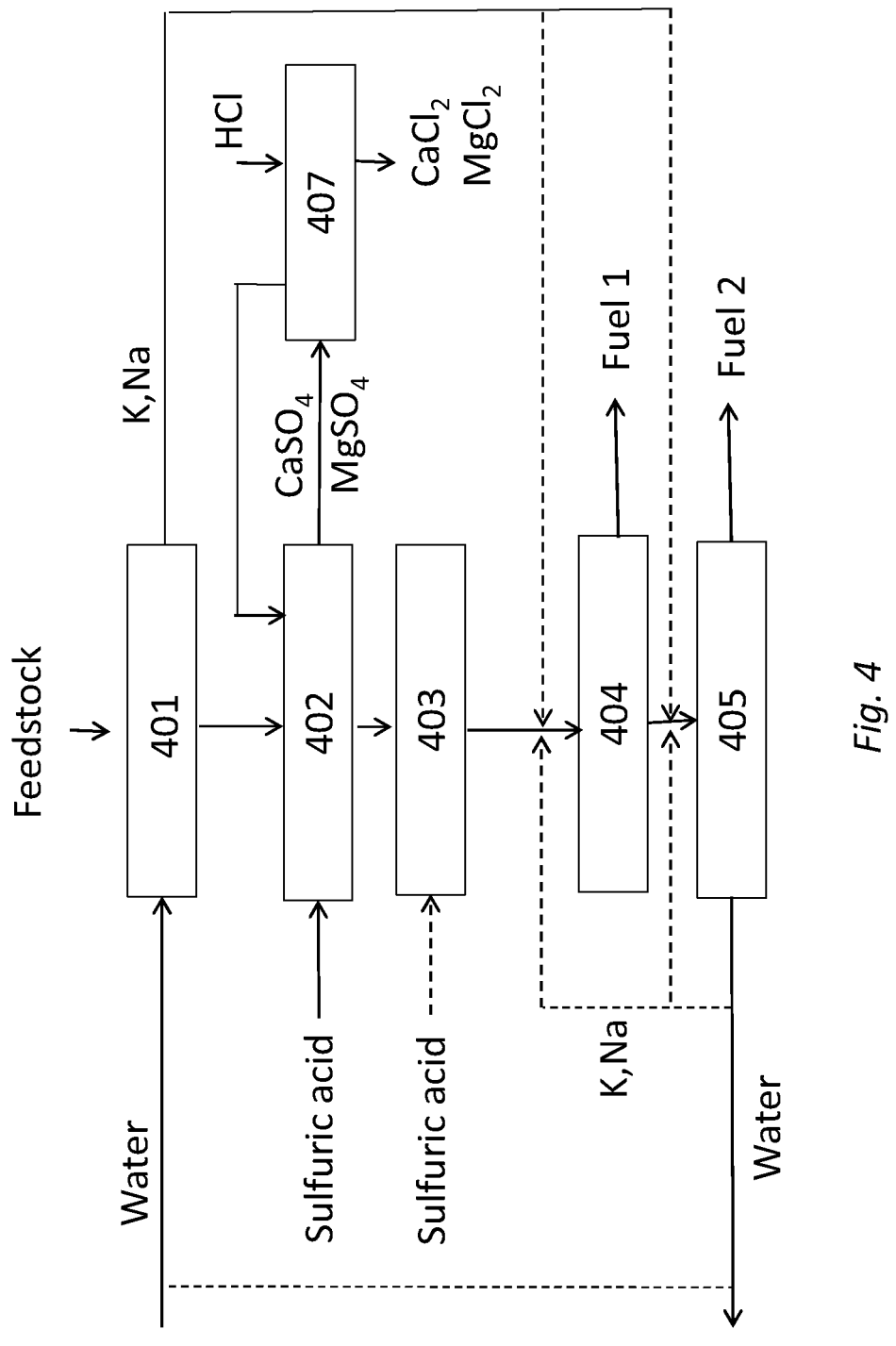
FIG. 4 is a flow diagram illustrating a process for producing fuel from lignocellulosic biomass in accordance with one embodiment.

Referring to FIG. 4 there is shown a flow diagram illustrating one embodiment of the invention. The lignocellulosic feedstock (i.e., wheat straw in this embodiment), which has been subject to a size reduction, is fed to a washing process 401 wherein it is washed with water using a water to dry feedstock ratio, by weight, of at least 3:1, at least 5:1, or at least 9:1. When the temperature of the wash water is 50° C., more than about 80% of the potassium is removed after about 20 minutes using a single stage wash. The washed feedstock is fed to the acid soaking process 402 wherein it is subjected to a three stage acid soaking process, wherein in each stage the soaking liquid is a sulfuric acid solution having a pH of about 3 and a temperature of about 50° C., and wherein the consistency is between about 3% and about 5% for the acid soaks and about 28% following each solids/liquid separation. This removes at least 80% of the minerals by weight, in aggregate, from the lignocellulosic feedstock. A mineralized soaking liquid, which contains the dissolved minerals (e.g., calcium and magnesium sulfate salts) is provided to cation exchange 407. Clean sulfuric acid solution produced by the cation exchange 407 is recycled to the acid soaking process 402. The demineralized feedstock is fed to pretreatment 403. In this embodiment, a small amount of supplemental sulfuric acid is added to reduce the pH from about 3 to between about 1.2 and about 1.8 for the pretreatment. At least part of the pretreated material (i.e., the cellulose) is converted to a first fermentation product in a first conversion process 404 that includes an enzymatic hydrolysis, a fermentation, and a fermentation product recovery. The fermentation product can be a fuel or used to produce a fuel. At least one secondary stream produced from the first conversion process 404 (e.g., at least part of the still bottoms and/or C5 sugars) is fed to an anaerobic digestor, such that another part of the pretreated material can be converted to fuel in the second conversion process 405. Accordingly, the fraction of the lignocellulosic feedstock converted to fuel is increased. Furthermore, since the acid soaking process 402 reduces the minerals in the lignocellulosic feedstock, and thus reduces the amount of sulfuric acid required for pretreatment 403, and carried through the first conversion process 404, more biogas can be produced (e.g., per BCOD) in the second conversion process 405. Accordingly, the fraction of the lignocellulosic feedstock that can be converted to fuel is further increased.

Advantageously, various embodiments of this process include recycle of the wash liquor from the washing process 401, which can contain an appreciable amount of potassium from the lignocellulosic feedstock (e.g., present as potassium carbonates), and/or the effluent from the anaerobic digestion in the second conversion 405, which can also contain an appreciable amount of potassium from the lignocellulosic feedstock.

In general, each of these streams, or part thereof, may be used for pH adjustment within the process. For example, in one embodiment, one or more of these streams are used adjust the pH of the pretreated material (e.g., solids and/or liquid) and/or to adjust the pH of the anaerobic digester and/or feeds thereto. Using some or all of these streams for pH adjustment can reduce costs (e.g., cost of alkali).

Alternatively, or additionally, each of these streams, or part thereof, may be used as a water source, may be further treated (e.g., aerobic digestion and/or reverse osmosis), and/or may be fed to waste disposal. For example, in one embodiment, effluent from the anaerobic digester is fed to aerobic digestion followed by reverse osmosis to remove the cations, or is fed to a cation exchange to remove the cations, before provided as incoming wash water to the water wash process 401. Using some or all of these streams as a water source can reduce water usage.

Advantageously, this process can have a relatively low water consumption, particularly when both the washing process and the acid soaking process are multi-stage countercurrent processes. Using multi-stage countercurrent washing significantly reduces water consumption. Using a multi-stage countercurrent acid soaking further reduces water consumption. For example, in addition to using less water for the acid soaking process, it can also reduce water usage downstream (e.g., facilitate pretreatment at a higher consistency).

Figure 5:
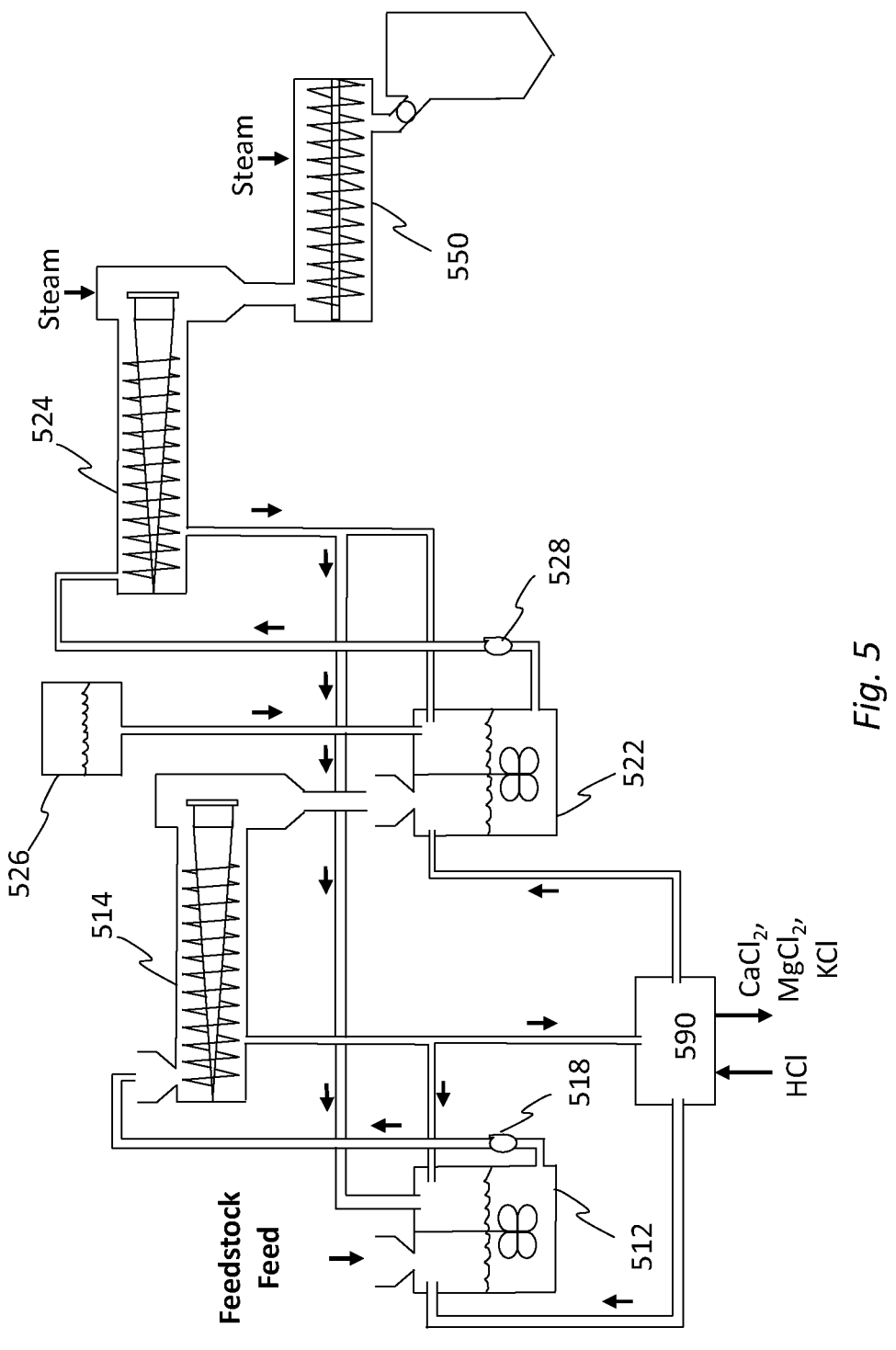
FIG. 5 is a schematic diagram illustrating a system for conducting a two-stage acid soak in accordance with one embodiment.

Referring to FIG. 5, there is shown a schematic diagram of an acid soaking system that can be used according to one embodiment of the invention. The acid soaking system includes a first continuous stirred vessel 512 configured to receive a lignocellulosic feedstock containing minerals (i.e., calcium and/or magnesium), a pump 518 for pumping acid soaked lignocellulosic feedstock slurry to a first screw press 514, which separates the feedstock from a least a portion of the soaking liquid, a second continuous stirred vessel 522 configured to receive the demineralized feedstock produced from the first screw press 514, and a pump 528 configured to pump acid soaked lignocellulosic feedstock slurry to the second screw press 524, which separates the feedstock from a least a portion of the soaking liquid. A cation exchange system 590 is configured to remove minerals from the mineralized soaking liquid produced from the first screw press 514, and to provide clean sulfuric acid solution to the first 512 and/or second 522 continuous stirred vessels. Make up-sulfuric acid 526 may also be provided as needed. In this embodiment, the first screw press 514 is an atmospheric screw press, whereas the second screw press is a pressurized screw press configured to provide the demineralized feedstock to the pressurized pretreatment reactor 550.

Figure 6:
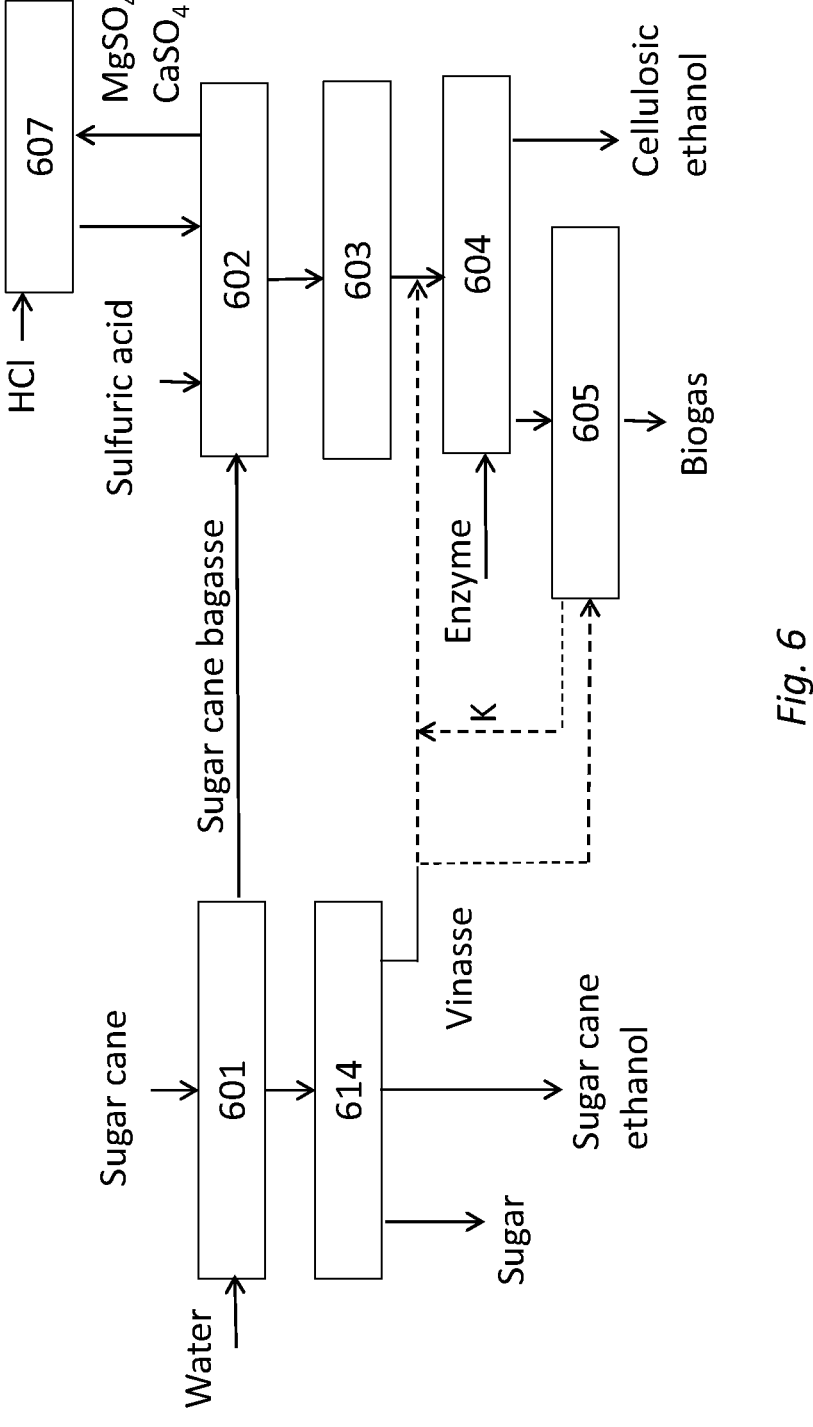
FIG. 6 is a flow diagram illustrating a process for producing fuel from lignocellulosic biomass in accordance with one embodiment; and, FIG. 7 is a plot showing the xylose concentration as a function of pretreatment time, when a demineralized feedstock is pretreated at 200° C.

Referring to FIG. 6, there is shown a flow diagram illustrating one embodiment of the invention, wherein the lignocellulosic feedstock is sugar cane. In this embodiment, the sugar cane is subjected to a milling process 601, which includes chopping and shredding the sugar cane, and then crushing the chopped/shredded sugar cane to extract the sugar cane juice. More specifically, it is crushed in milling rolls (e.g., a train of 3-6 cane presses), which are provided with a countercurrent wash system. Hot water used to wash the chopped/shredded sugar cane that passes through the last cane press in the train is collected and used to wash the chopped/shredded cane that passes through the penultimate cane press in the train. At the end of the train, a washed solid waste-product, which is known as bagasse, is provided. A mixed juice, containing the wash liquor and cane juice is withdrawn from one or more cane presses near the beginning of the train. The juice is processed 614 to produce raw sugar, molasses, and/or ethanol, as familiar to those skilled in the art. For example, raw sugar and molasses can be produced in a process including filtering, lime addition, pasteurization (heating), clarification, evaporation, crystallization, and/or centrifugation. In this embodiment, the molasses are fermented to ethanol, which is recovered by distillation. The distillation produces vinasse, which can have a relatively high organic matter concentration and/or mineral content (e.g., potassium).

As an appreciable amount of potassium is removed from the sugar cane as a result of the washing process, the washed bagasse produced by the milling process can be provided as feed to the acid soaking process 602 without additional washing. In this embodiment, the acid soaking process 602 is a two-stage acid soaking process. In each stage the soaking liquid is a sulfuric acid solution, the temperature of the soaking liquid is about 50° C., the soak is conducted at a consistency between about 3% and about 5%, and the solids/liquid separation provides a demineralized feedstock having a consistency between about 24% and about 28%. The first soaking stage is conducted at a pH of about 3 and the second stage at a pH of about 1.8. A mineralized soaking liquid, which contains the dissolved minerals (e.g., calcium and magnesium sulfate salts) is provided to cation exchange 607. Clean sulfuric acid solution produced by the cation exchange 607 is recycled to the acid soaking process 602. The demineralized feedstock is fed to pretreatment 603. In this embodiment, no supplemental sulfuric acid is required to reduce the pH for pretreatment 603, which is conducted at pH 1.8. At least part of the pretreated material (i.e., the cellulose) is converted to ethanol in a first conversion process 604 that includes an enzymatic hydrolysis, a fermentation, and a distillation. The distillation produces still bottoms, which are subjected to a solid liquid separation. The solids are fed to a boiler (not shown). The liquid is fed to an anerobic digestion as part of a second conversion process 605, which produces biogas.

In one embodiment, the vinasse, or part thereof, is used for pH adjustment purposes within the process (e.g., vinasse can have a significant potassium content). In one embodiment, at least part of the vinasse is used to adjust the pH of the pretreated material from pretreatment 603. For example, in one embodiment, at least part of the vinasse, which may be acidic, is heat-treated to increase the pH thereof (e.g., in an evaporation that removes acetic acid), and the alkaline and concentrated vinasse is mixed with at least part of the pretreated material (i.e., liquids and/or solids) upstream of and/or as part of enzymatic hydrolysis and/or fermentation. Accordingly, the potassium in the vinasse is carried through to the still bottoms. The still bottoms and/or at least part of the vinasse is fed to the anaerobic digester. In one embodiment, the effluent from the digester is heat treated (e.g., to drive off carbon dioxide from potassium bicarbonate, thereby producing potassium carbonate), and the treated effluent, which contains potassium originating from the vinasse, is used for pH adjustment of at least part of the pretreated material. Advantageously, this process produces sugarcane ethanol, cellulosic ethanol, and biogas. Thereby, producing more fuel from a given amount of feedstock.

EXAMPLES

Example 1

Wheat straw was sourced in Ottawa, Ontario and consists of 10% moisture, by weight. It was hammer-milled to ½-inch particles. The concentration of the minerals in the straw was determined using ICP-OES and is listed in Table 1.

TABLE 1

| | | Minerals in the wheat straw | |
| --- | --- | --- | --- |
| Element | Symbol | Concentration (mg/kg, dry basis) | % of Total Minerals |
| Potassium | K | 6686 | 52 |
| Calcium | Ca | 2789 | 22 |
| Magnesium | Mg | 1008 | 8 |
| Iron | Fe | 1845 | 14 |
| Aluminum | A | 558 | 4 |
| Sodium | Na | 86 | <1 |
| Total | | 12972 | |

The wheat straw was subjected to a washing process, wherein it was washed with water to remove the potassium. The washing process was conducted by suspending the wheat straw in deionized water at a consistency of 3% in a 250-ml shake flask (100 g total weight). The flask was shaken at 200 rpm, 50° C. for 60 minutes. At the end of this period, the slurry was transferred to a 150 ml syringe and pressed to 28% consistency. The pressed straw cake was resuspended in deionized water to 3% consistency and the procedure repeated. The resulting second straw cake had more than 95% of the potassium removed, with the other minerals largely unaffected.

The washed feedstock was then subjected to an acid soaking process, wherein it was soaked in an aqueous sulfuric acid solution to remove minerals that were not dissolved in the water wash (e.g., water insoluble). The acid soaking process was conducted in a single-stage acid soak, by soaking the washed 28% consistency straw in a 0.00313 M sulfuric acid having a pH of 2.30. The acid soaking was carried out at 3% consistency in a 250 mL flask shaken at 200 RPM at 50° C. for 1 hr. After this period, the straw was pressed by using a similar syringe as was used in the water wash, to yield a solids cake having a consistency of 28%. The 28% solids cake contained 388.9 g solids/L liquor. The final pH of the solids and pressate was 3.00. The pressate, which is an aqueous liquor containing sulfuric acid and dissolved minerals, is suitable for cation exchange.

The concentration of minerals in the straw after the acid soak is listed in Table 2. A majority of cations have been removed from the straw by the water wash and acid soak, with only an aggregate of about 10% remaining.

TABLE 2

| | Minerals in the wheat straw after acid soaks | | |
| --- | --- | --- | --- |
| Element | Concentration (mg/kg) in original feedstock | Concentration (mg/kg) in demineralized feedstock | % Removed |
| Potassium | 6686 | 50 | 99 |
| Calcium | 2789 | 550 | 80 |
| Magnesium | 1008 | 290 | 71 |
| Iron | 1845 | 290 | 84 |
| Aluminum | 558 | 130 | 76 |
| Sodium | 86 | 50 | 42 |
| Total | 12972 | 1360 | 90 |

Figure 7:
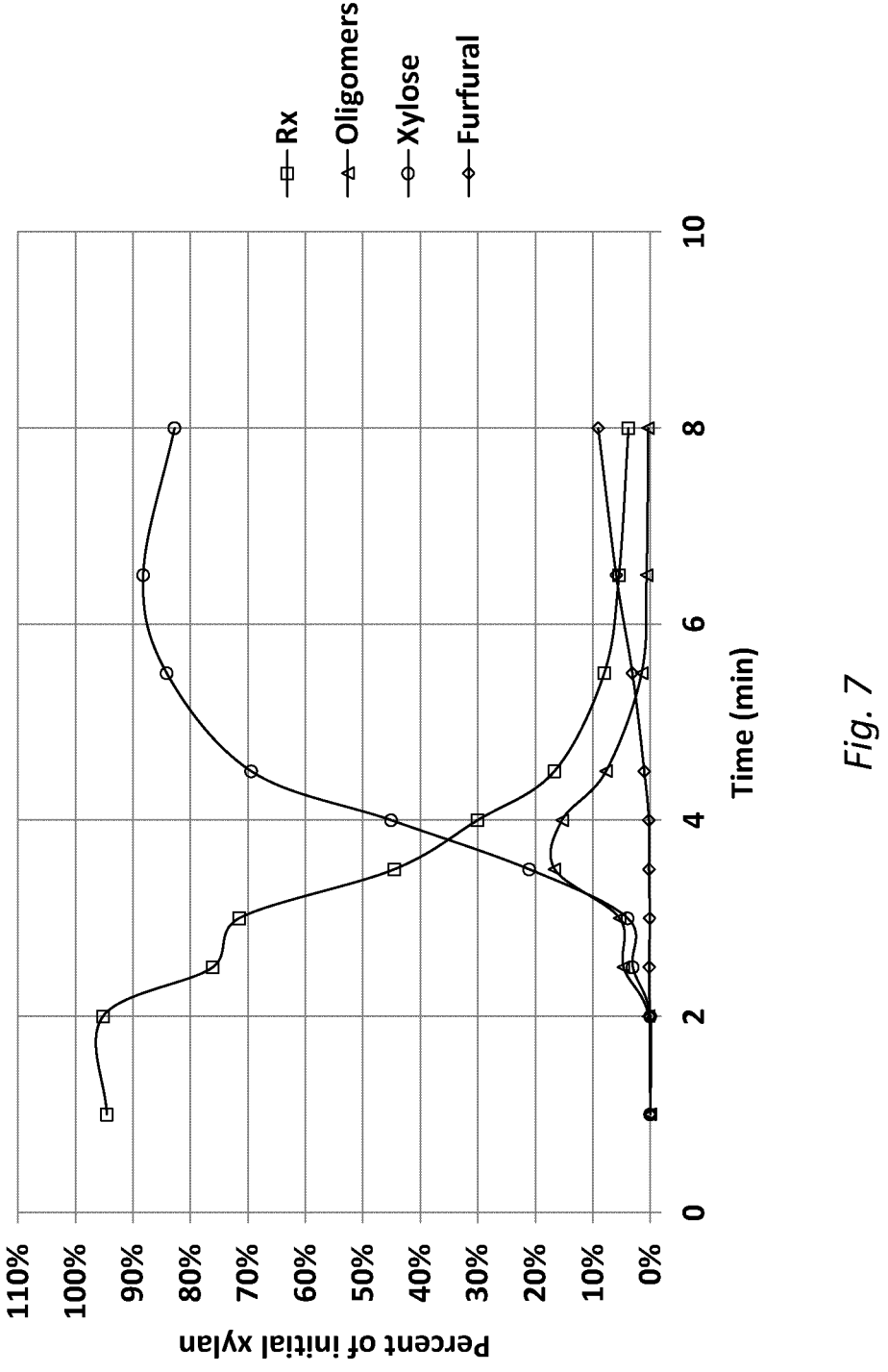

The pressed cakes from the acid soaks were pretreated in 25-ml laboratory "bomb" pretreatment reactors. For each pretreatment, about 0.9 g of wet acidified cake was added to acidic water to make a total of 15 grams slurry at 0.0119 M H₂SO₄ (pH 1.8). This was placed in the reactor, which was then submerged in a 200° C. oil bath for a period of 1 to 8 minutes. After that time, the reactor was placed in ice water to cool down quickly. Once cooled, the reactors were opened and the contents assayed for residual xylan by an in-house carbohydrate method derived from the NREL method (Determination of Carbohydrates and Lignin in Biomass LAP) and analyzed for xylose, furfural, and xylo-oligomers of 2 to 4 monomers by using a Dionex HPLC with a PAI Carbopac anion exchange column and PAD detection. The initial xylan concentration of the straw was 21.33%. The results are shown in FIG. 7. The yield of xylose reached 89% at 6.5 minutes, which is impressive.

Example 2

Wheat straw from the same source as Example 1 (i.e., see Table 1) was subjected to a washing process, wherein it was washed with water to remove the potassium. The washing process was conducted by suspending the wheat straw in deionized water at a consistency of 3% in a 250 mL shake flask (100 g total weight). The flask was shaken at 200 rpm, 50° C. for 60 minutes. At the end of this period, the slurry was transferred to a 150 mL syringe and pressed to 28% consistency. The pressed straw cake was resuspended in deionized water to 3% consistency and the procedure repeated. The resulting second straw cake had more than 95% of the potassium removed, with the other minerals largely unaffected.

The washed feedstock was then subjected to an acid soaking process, wherein it was soaked in an aqueous sulfuric acid solution to remove minerals that were not dissolved in the water wash. The acid soaking process was conducted in a two-stage acid soak.

In the first stage, the washed, 28% consistency straw was soaked in a 0.0130 M sulfuric acid having a pH of 1.8. The acid soaking was carried out at 3% consistency in a 250 mL flask shaken at 200 RPM at 50° C. for 1 hr. After this period, the straw was pressed by using a similar syringe as was used in the water wash, to yield a solids cake having a consistency of 28%. The 28% solids cake contained 388.9 g solids/L liquor. The final pH of the solids and pressate was 1.81. The pressate, which is an aqueous liquor containing sulfuric acid and dissolved minerals, is suitable for cation exchange.

In the second stage, the pressed cake was soaked for a second time in a 0.0130 M sulfuric acid solution having a pH of 1.8. The acid soaking in this second stage was carried out at 3% consistency in a 250 mL flask shaken at 200 RPM at 50° C. for 1 hr. After this period, the straw was pressed by using a similar syringe as was used in the water wash, to yield a solids cake having a consistency of 28%. As with the first acid soak, the pressate from the second acid soak is suitable for cation exchange. As the solids cake is at pH 1.75, little to no further acid may be needed for pretreatment.

The pressed cakes from the acid soaks were pretreated in 25-ml laboratory "bomb" pretreatment reactors. For each pretreatment, about 2.2 g of wet acidified cake was placed in the reactor, which was then submerged in a 200° C. oil bath for a period of 6.5 to 8.5 minutes. After that time, the reactor was placed in ice water to cool down quickly.

Advantageously, these pretreatments were achieved using a relatively low sulfuric acid loading. The amount of sulfuric acid that was carried through from the first acid soak to the second acid soak and from the second acid soak to pretreatment, in this example, was calculated as 0.26 g sulfuric acid/kg solids and 3.27 g sulfuric acid/kg solids, respectively. These values were converted to kg/t and added to yield a total sulfuric acid loading as 3.53 kg sulfuric acid/ton of dry feedstock, as illustrated in Table 3.

TABLE 3

| Sulfuric acid usage in pretreatment | |
| --- | --- |
| Acid Soak | Sulfuric acid (kg/t) |
| Stage 1 | 0.26 |
| Stage 2 | 3.27 |
| Total | 3.53 |

Advantageously, a sulfuric acid loading of 3.53 kg $H_2SO_4$/ton of dry feedstock is relatively low. Providing less than about 12 kg $H_2SO_4$/ton of dry lignocellulosic biomass for pretreatment can be advantageous for the downstream anerobic digestion.

Of course, the above embodiments have been provided as examples only. It will be appreciated by those of ordinary skill in the art that various modifications, alternate configurations, and/or equivalents will be employed without departing from the spirit and scope of the invention. Accordingly, the scope of the invention is therefore intended to be limited solely by the scope of the appended claims.

The invention claimed is:

1. A process for converting lignocellulosic biomass to fuel, said process comprising:
    (a) a demineralization, said demineralization comprising subjecting a feedstock to an acid soaking process, said feedstock comprising the lignocellulosic biomass, said acid soaking process comprising one or more acid soak stages, wherein each of the one or more acid soak stages comprises (i) contacting the feedstock with a soaking liquid to produce a soaked feedstock slurry, and (ii) subjecting the soaked feedstock slurry to a solids/liquid separation, wherein the soaking liquid in each of the one or more acid soak stages is an aqueous solution comprising sulfuric acid having a pH between 1 and 5;
    (b) a pretreatment, said pretreatment comprising heating a slurry containing sulfuric acid and demineralized feedstock produced from the demineralization, said heating conducted at a temperature between 150° C. and 230° C. and at a pH between 1 and 2.5, said pretreatment producing a pretreated slurry;
    (c) a first conversion, said first conversion comprising an enzymatic hydrolysis wherein cellulose in the pretreated slurry is converted to glucose, a fermentation wherein the glucose is converted to a fermentation product, and a fermentation product recovery, wherein the first conversion produces a secondary stream that contains one or more sulfur compounds derived from sulfuric acid used in the demineralization, the sulfuric acid used in pretreatment, or a combination thereof;
    (d) a second conversion, said second conversion comprising feeding at least part of the secondary stream to an anaerobic digester and collecting biogas from the anaerobic digester, said biogas used as a fuel within the process, processed to provide a fuel, or a combination thereof, and
    (e) a recycling process, said recycling process comprising feeding mineralized soaking liquid produced from step (a) to cation exchange wherein minerals are removed, and feeding clean sulfuric acid solution produced from the cation exchange to at least one acid soak stage in step (a).

2. The process according to claim 1, wherein the acid soaking process comprises a multi-stage countercurrent acid soak.

3. The process according to claim 2, wherein a pressate recycle fraction in at least one of the stages of the acid soaking process is greater than 10%.

4. The process according to claim 1, wherein the feedstock subjected to the acid soaking process has had at least 75% of the potassium originally present removed.

5. The process according to claim 1, wherein the conditions for the acid soaking process are selected to remove at least 70% of the calcium originally present in the lignocellulosic biomass.

6. The process according to claim 1, wherein the soaking liquid in each of the one or more acid soak stages has a pH between 1.2 and 4 and is at a temperature between 30° C. and 90° C.

7. The process according to claim 1, wherein step (i) of each acid soak stage is conducted at a consistency between 2% and 10% for at least 5 minutes.

8. The process according to claim 1, wherein step (ii) of each acid soak stage provides solids having a consistency of at least 15%.

9. The process according to claim 1, comprising a washing process upstream of the acid soaking process, said washing process comprising one or more washing stages, wherein each of the one or more washing stages comprises (a) contacting the feedstock with a wash water, and (b) a solids/liquid separation wherein the feedstock is separated from at least a portion of the wash water, wherein the conditions for the washing process are selected to remove at least 70% of the potassium originally present in the feedstock.

10. The process according to claim 1, wherein the secondary stream comprises at least part of still bottoms from the fermentation product recovery.

11. The process according to claim 10, wherein the still bottoms are subjected to a solids/liquid separation that provides solids and liquids, where the secondary stream comprises liquid produced from the solids/liquid separation of the still bottoms.

12. The process according to claim 1, wherein the first conversion comprises subjecting the pretreated slurry to a solids/liquid separation, and wherein the secondary stream comprises liquid from the solids/liquid separation of the pretreated slurry.

13. The process according to claim 1, wherein the enzymatic hydrolysis in the first conversion is conducted on unwashed demineralized feedstock.

14. The process according to claim 1, wherein the fermentation product is ethanol.

15. The process according to claim 1, wherein the second conversion comprises producing renewable natural gas from the biogas.

16. The process according to claim 1, wherein the amount of sulfuric acid provided in pretreatment is not more than 12 kg $H_2SO_4$/ton of dry lignocellulosic biomass.

17. The process according to claim 1, wherein the secondary stream has a sulfate concentration that is not more than 5 g/L.

18. The process according to claim 1, wherein the secondary stream has a biologically degraded chemical oxygen demand to sulfate ratio of at least 7 to 1.

19. A process for converting lignocellulosic biomass to fuel, said process comprising:

subjecting a feedstock comprising lignocellulosic biomass to a washing process to provide a washed feedstock, subjecting the washed feedstock to an acid soaking process to produce a demineralized feedstock, said acid soaking process comprising a multi-stage countercurrent acid soak, each stage of the multi-stage acid soak comprising (a) contacting the feedstock with an aqueous sulfuric acid solution having a pH not more than 3, and (ii) a solids/liquid separation that provides a pressate and solids, said solids having a consistency of at least 20%, wherein a pressate recycle fraction in at least one stage of the multi-stage countercurrent acid soak is greater than 10% by weight;

pretreating the demineralized feedstock to produce a pretreated slurry comprising cellulose, said pretreating comprising heating a slurry containing sulfuric acid and the demineralized feedstock at a temperature between 150° C. and 230° C. and at a pH between 1 and 2.5;

converting at least part of the pretreated slurry to ethanol, said converting comprising hydrolyzing the cellulose to glucose in an enzymatic hydrolysis, fermenting the glucose to ethanol, and recovering the ethanol in a distillation that produces concentrated ethanol and still bottoms;

feeding a stream comprising at least part of the still bottoms to an anaerobic digestion, said stream comprising sulfate derived from sulfuric acid used in the acid soaking process, sulfate derived from sulfuric acid used in pretreatment, or a combination thereof;

collecting biogas from the anaerobic digester, said collected biogas used as a fuel within the process, processed to provide a transportation fuel, or a combination thereof; and subjecting mineralized soaking liquid produced from the acid soaking process to cation exchange to remove one or more minerals therefrom and recycling clean sulfuric acid solution produced by cation exchange within the acid soaking process.

* * * * *